US008945079B2

(12) United States Patent
Sauer et al.

(10) Patent No.: US 8,945,079 B2
(45) Date of Patent: *Feb. 3, 2015

(54) DISPOSABLE WEARABLE ABSORBENT ARTICLES WITH ANCHORING SUBSYSTEMS

(75) Inventors: Andrew James Sauer, Cincinnati, OH (US); Michael Dale Trennepohl, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 565 days.

This patent is subject to a terminal disclaimer.

(21) Appl. No.: 12/204,849

(22) Filed: Sep. 5, 2008

(65) Prior Publication Data

US 2009/0069782 A1    Mar. 12, 2009

Related U.S. Application Data

(63) Continuation-in-part of application No. 11/899,812, filed on Sep. 7, 2007.

(51) Int. Cl.
*A61F 13/15* (2006.01)
*A61F 13/56* (2006.01)
*A61F 13/49* (2006.01)

(52) U.S. Cl.
CPC ....... *A61F 13/5622* (2013.01); *A61F 13/49014* (2013.01)
USPC ..................................... 604/385.22; 604/386

(58) Field of Classification Search
USPC ................ 604/385.24, 385.27, 389
See application file for complete search history.

(56) References Cited

U.S. PATENT DOCUMENTS

| | | |
|---|---|---|
| 84,703 A | 12/1868 | Moore |
| 1,157,774 A | 10/1914 | Goodnou |
| 1,485,001 A | 2/1924 | Wills |
| 1,487,154 A | 3/1924 | Deloris et al. |
| 1,609,769 A | 12/1926 | Perlzweig |
| 1,611,936 A | 3/1928 | Ferstl |
| 1,702,194 A | 3/1929 | Marinsky |
| 1,756,508 A | 4/1930 | Bersin |
| 1,917,979 A | 7/1933 | Kelly |
| 2,025,843 A | 12/1935 | Anderson |

(Continued)

FOREIGN PATENT DOCUMENTS

| | | |
|---|---|---|
| EP | 0 323 634 A2 | 12/1989 |
| EP | 0 858 787 | 8/1998 |

(Continued)

*Primary Examiner* — Melanie Hand
(74) *Attorney, Agent, or Firm* — Kathleen Y. Carter; John G. Powell; Charles R. Ware

(57) ABSTRACT

A disposable wearable absorbent article comprising an absorbent core area, a side, and an anchoring subsystem. The anchoring subsystem includes exactly one side anchoring member. The side anchoring member has a pathway with a front end, a back end, and a middle. The front end, the back end, or both ends are disposed outside of the absorbent core area. The front end is disposed at a front end longitudinally outboard distance. The back end is disposed at a back end longitudinally outboard distance. The middle is disposed at a middle longitudinally outboard distance. The back end longitudinally outboard distance is less than the front end longitudinally outboard distance. The front end longitudinally outboard distance is about equal to the middle longitudinally outboard distance.

16 Claims, 16 Drawing Sheets

(56) References Cited

U.S. PATENT DOCUMENTS

| | | |
|---|---|---|
| 2,126,905 A | 8/1938 | Englander et al. |
| 2,413,970 A | 1/1947 | Hawley, Jr. |
| 2,493,113 A | 1/1950 | Dance |
| 2,572,331 A | 10/1951 | Gilessen |
| 2,652,058 A | 9/1953 | Carpenter |
| 2,699,171 A | 1/1955 | McWilliams |
| 3,441,025 A | 4/1969 | Ralph |
| 3,635,221 A | 1/1972 | Champaigne |
| 3,658,064 A | 4/1972 | Pociluyko |
| 3,692,618 A | 9/1972 | Dorschner et al. |
| 3,802,817 A | 4/1974 | Matsuki et al. |
| 3,825,006 A | 7/1974 | Ralph |
| 3,848,594 A | 11/1974 | Buell |
| 3,860,003 A | 1/1975 | Buell |
| 3,911,173 A | 10/1975 | Sprague, Jr. |
| 3,929,135 A | 12/1975 | Thompson |
| 4,116,892 A | 9/1978 | Schwarz |
| 4,209,016 A | 6/1980 | Schaar |
| 4,315,508 A | 2/1982 | Bolick |
| 4,324,246 A | 4/1982 | Mullane et al. |
| 4,340,563 A | 7/1982 | Appel et al. |
| 4,342,314 A | 8/1982 | Radel et al. |
| 4,381,781 A | 5/1983 | Sciaraffa et al. |
| 4,463,045 A | 7/1984 | Ahr et al. |
| 4,515,595 A | 5/1985 | Kievit et al. |
| 4,573,986 A | 3/1986 | Minetola et al. |
| 4,609,518 A | 9/1986 | Curro et al. |
| 4,610,678 A | 9/1986 | Weisman et al. |
| 4,629,643 A | 12/1986 | Curro et al. |
| 4,655,760 A | 4/1987 | Morman et al. |
| 4,662,875 A | 5/1987 | Hirotsu et al. |
| 4,673,402 A | 6/1987 | Weisman et al. |
| 4,695,278 A | 9/1987 | Lawson |
| 4,699,621 A | 10/1987 | Stevens et al. |
| 4,701,171 A | 10/1987 | Boland et al. |
| 4,701,172 A | 10/1987 | Stevens |
| 4,701,173 A | 10/1987 | Zehner et al. |
| 4,701,174 A | 10/1987 | Johnson |
| 4,701,175 A | 10/1987 | Boland et al. |
| 4,710,189 A | 12/1987 | Lash |
| 4,718,900 A | 1/1988 | Boland et al. |
| 4,720,415 A | 1/1988 | VanderWielen et al. |
| 4,756,709 A | 7/1988 | Stevens |
| 4,770,656 A | 9/1988 | Proxmire et al. |
| 4,785,996 A | 11/1988 | Ziecker et al. |
| 4,795,454 A | 1/1989 | Dragoo |
| 4,808,178 A | 2/1989 | Aziz et al. |
| 4,816,025 A | 3/1989 | Foreman |
| 4,834,735 A | 5/1989 | Alemany et al. |
| 4,834,738 A | 5/1989 | Kielpikowski et al. |
| 4,834,741 A | 5/1989 | Sabee |
| 4,838,885 A | 6/1989 | Bernardin |
| 4,842,666 A | 6/1989 | Werenicz |
| 4,846,815 A | 7/1989 | Scripps |
| 4,850,990 A | 7/1989 | Huntoon et al. |
| 4,850,992 A | 7/1989 | Amaral et al. |
| 4,857,067 A | 8/1989 | Wood et al. |
| 4,865,823 A | 9/1989 | Minagawa et al. |
| 4,869,724 A | 9/1989 | Scripps |
| 4,888,231 A | 12/1989 | Angstadt |
| 4,892,536 A | 1/1990 | Desmarais et al. |
| 4,894,060 A | 1/1990 | Nestegard |
| 4,909,803 A | 3/1990 | Aziz et al. |
| 4,938,753 A | 7/1990 | Van Gompel et al. |
| 4,940,464 A | 7/1990 | Van Gompel et al. |
| 4,946,527 A | 8/1990 | Battrell |
| 4,962,571 A | 10/1990 | Visser |
| 4,963,140 A | 10/1990 | Robertson et al. |
| 4,968,312 A | 11/1990 | Khan |
| 4,988,344 A | 1/1991 | Reising et al. |
| 4,988,345 A | 1/1991 | Reising |
| 4,990,147 A | 2/1991 | Freeland |
| 4,995,873 A | 2/1991 | Knight |
| 5,006,394 A | 4/1991 | Baird |
| 5,026,364 A | 6/1991 | Robertson |
| 5,037,416 A | 8/1991 | Allen et al. |
| 5,062,840 A | 11/1991 | Holt et al. |
| 5,069,672 A | 12/1991 | Wippler |
| 5,077,868 A | 1/1992 | Visser |
| 5,092,861 A | 3/1992 | Nomura et al. |
| 5,137,537 A | 8/1992 | Herron et al. |
| 5,143,679 A | 9/1992 | Weber et al. |
| 5,147,345 A | 9/1992 | Young et al. |
| 5,151,092 A | 9/1992 | Buell et al. |
| 5,156,793 A | 10/1992 | Buell et al. |
| 5,167,897 A | 12/1992 | Weber et al. |
| 5,171,236 A | 12/1992 | Dreier et al. |
| 5,171,239 A | 12/1992 | Igaue et al. |
| 5,217,447 A | 6/1993 | Gagnon |
| 5,221,274 A | 6/1993 | Buell et al. |
| 5,246,433 A | 9/1993 | Hasse et al. |
| 5,260,345 A | 11/1993 | Desmarais et al. |
| 5,269,775 A | 12/1993 | Freeland et al. |
| 5,304,162 A | 4/1994 | Kuen |
| 5,306,266 A | 4/1994 | Freeland |
| 5,318,555 A | 6/1994 | Siebers et al. |
| 5,342,338 A | 8/1994 | Roe |
| 5,358,500 A | 10/1994 | LaVon et al. |
| 5,366,782 A | 11/1994 | Curro et al. |
| 5,374,262 A | 12/1994 | Keuhn et al. |
| 5,380,313 A | 1/1995 | Goulait et al. |
| 5,386,595 A | 2/1995 | Kuen et al. |
| 5,387,207 A | 2/1995 | Dyer et al. |
| 5,397,318 A | 3/1995 | Dreier |
| 5,399,177 A | 3/1995 | Blaney et al. |
| 5,405,682 A | 4/1995 | Shawyer et al. |
| 5,407,439 A | 4/1995 | Goulait |
| 5,411,498 A | 5/1995 | Fahrenkrug et al. |
| 5,422,172 A | 6/1995 | Wu |
| 5,423,789 A | 6/1995 | Kuen |
| 5,433,826 A | 7/1995 | Glomb et al. |
| 5,458,592 A | 10/1995 | Abuto et al. |
| 5,470,639 A | 11/1995 | Gessner et al. |
| 5,514,121 A | 5/1996 | Roe et al. |
| 5,518,801 A | 5/1996 | Chappell et al. |
| 5,540,671 A | 7/1996 | Dreier |
| 5,540,673 A | 7/1996 | Thomas et al. |
| 5,540,976 A | 7/1996 | Shawver et al. |
| 5,542,942 A | 8/1996 | Kline et al. |
| 5,554,142 A | 9/1996 | Dreier et al. |
| 5,554,145 A | 9/1996 | Roe et al. |
| 5,562,646 A | 10/1996 | Goldman et al. |
| 5,569,233 A | 10/1996 | Goulait |
| 5,569,234 A | 10/1996 | Buell et al. |
| 5,571,096 A | 11/1996 | Dobrin et al. |
| 5,580,411 A | 12/1996 | Nease et al. |
| 5,595,567 A | 1/1997 | King et al. |
| 5,607,416 A | 3/1997 | Yamamoto et al. |
| 5,607,537 A | 3/1997 | Johnson et al. |
| 5,607,760 A | 3/1997 | Roe |
| 5,609,587 A | 3/1997 | Roe |
| 5,620,431 A | 4/1997 | LeMahieu et al. |
| 5,622,589 A | 4/1997 | Johnson et al. |
| 5,624,427 A | 4/1997 | Bergman et al. |
| 5,625,222 A | 4/1997 | Yoneda et al. |
| 5,634,917 A | 6/1997 | Fujioka et al. |
| 5,635,191 A | 6/1997 | Roe et al. |
| 5,635,290 A | 6/1997 | Stopper et al. |
| 5,635,588 A | 6/1997 | Eshuis et al. |
| H1670 H | 7/1997 | Aziz et al. |
| 5,643,239 A | 7/1997 | Bodford et al. |
| 5,643,242 A | 7/1997 | LaVon et al. |
| 5,643,588 A | 7/1997 | Roe et al. |
| 5,650,222 A | 7/1997 | DesMarais et al. |
| 5,653,703 A | 8/1997 | Roe et al. |
| 5,662,638 A | 9/1997 | Johnson et al. |
| 5,669,894 A | 9/1997 | Goldman et al. |
| 5,669,897 A | 9/1997 | LaVon et al. |
| 5,669,900 A | 9/1997 | Bullwinkel et al. |
| 5,669,901 A | 9/1997 | LaFortune et al. |
| 5,674,216 A | 10/1997 | Buell et al. |
| 5,691,035 A | 11/1997 | Chappell et al. |
| 5,695,849 A | 12/1997 | Shawver et al. |
| 5,700,256 A | 12/1997 | Yamamoto et al. |

(56) References Cited

U.S. PATENT DOCUMENTS

| | | | |
|---|---|---|---|
| 5,723,087 A | 3/1998 | Chappell et al. | |
| 5,735,840 A | 4/1998 | Kiline et al. | |
| 5,749,865 A | 5/1998 | Yamamoto et al. | |
| 5,772,825 A | 6/1998 | Schmitz | |
| 5,776,123 A | 7/1998 | Goerg et al. | |
| 5,779,831 A | 7/1998 | Schmitz | |
| 5,797,824 A | 8/1998 | Tracy | |
| 5,865,823 A | 2/1999 | Curro | |
| 5,873,870 A | 2/1999 | Seitz et al. | |
| 5,885,681 A | 3/1999 | Korpman | |
| 5,891,544 A | 4/1999 | Chappell et al. | |
| 5,897,545 A | 4/1999 | Kline et al. | |
| 5,899,895 A * | 5/1999 | Robles et al. | 604/385.29 |
| 5,916,206 A | 6/1999 | Otsubo et al. | |
| 5,916,661 A | 6/1999 | Benson et al. | |
| 5,916,663 A | 6/1999 | Chappell et al. | |
| 5,928,212 A | 7/1999 | Kline et al. | |
| 5,938,648 A | 8/1999 | Lavon et al. | |
| 5,941,864 A | 8/1999 | Roe | |
| 5,941,865 A | 8/1999 | Otsubo et al. | |
| 5,944,707 A | 8/1999 | Ronn | |
| 5,947,944 A | 9/1999 | Hetzler et al. | |
| 5,952,252 A | 9/1999 | Shawver et al. | |
| 5,957,908 A | 9/1999 | Kline et al. | |
| 5,997,521 A | 12/1999 | Robles et al. | |
| 5,997,989 A | 12/1999 | Gessner et al. | |
| 6,001,460 A | 12/1999 | Morman et al. | |
| 6,004,306 A | 12/1999 | Robles et al. | |
| 6,010,491 A | 1/2000 | Roe et al. | |
| 6,013,589 A | 1/2000 | DesMarais et al. | |
| 6,015,764 A | 1/2000 | Mccormack et al. | |
| 6,027,483 A | 2/2000 | Chappell et al. | |
| 6,042,673 A | 3/2000 | Johnson et al. | |
| 6,096,668 A | 8/2000 | Abuto et al. | |
| 6,103,647 A | 8/2000 | Shultz et al. | |
| 6,107,537 A | 8/2000 | Elder et al. | |
| 6,120,487 A | 9/2000 | Ashton | |
| 6,120,489 A | 9/2000 | Johnson et al. | |
| 6,132,409 A | 10/2000 | Vogt et al. | |
| 6,156,424 A | 12/2000 | Taylor | |
| 6,168,584 B1 | 1/2001 | Allen et al. | |
| 6,168,585 B1 | 1/2001 | Cesco-Cancian | |
| 6,169,151 B1 | 1/2001 | Waymouth et al. | |
| 6,179,820 B1 | 1/2001 | Fernfors | |
| 6,193,701 B1 | 2/2001 | Van Gompel et al. | |
| 6,225,243 B1 | 5/2001 | Austin | |
| 6,251,097 B1 | 6/2001 | Kline et al. | |
| 6,264,641 B1 | 7/2001 | Van Gompel et al. | |
| 6,303,208 B1 | 10/2001 | Pelkie | |
| 6,306,121 B1 | 10/2001 | Damaghi et al. | |
| 6,313,372 B1 | 11/2001 | Suzuki | |
| 6,364,863 B1 | 4/2002 | Yamamoto et al. | |
| 6,383,431 B1 | 5/2002 | Dobrin et al. | |
| 6,413,249 B1 | 7/2002 | Turi et al. | |
| 6,414,215 B1 | 7/2002 | Roe | |
| 6,423,043 B1 | 7/2002 | Gustafsson | |
| 6,432,098 B1 | 8/2002 | Kline et al. | |
| 6,436,512 B1 | 8/2002 | Kauschke et al. | |
| 6,437,214 B1 | 8/2002 | Everett et al. | |
| 6,441,266 B1 | 8/2002 | Dyer et al. | |
| 6,448,467 B1 | 9/2002 | Herrlein et al. | |
| 6,465,073 B1 | 10/2002 | Morman et al. | |
| 6,479,154 B1 | 11/2002 | Walton et al. | |
| 6,482,191 B1 | 11/2002 | Roe et al. | |
| 6,498,284 B1 | 12/2002 | Roe | |
| 6,503,236 B1 | 1/2003 | Uitenbroek et al. | |
| 6,518,378 B2 | 2/2003 | Waymouth et al. | |
| 6,531,027 B1 | 3/2003 | Lender et al. | |
| 6,547,774 B2 | 4/2003 | Ono et al. | |
| 6,555,643 B1 | 4/2003 | Rieger | |
| 6,559,262 B1 | 5/2003 | Waymouth et al. | |
| 6,573,423 B1 | 6/2003 | Herrlein et al. | |
| 6,579,274 B1 | 6/2003 | Morman et al. | |
| 6,585,713 B1 | 7/2003 | LeMahieu et al. | |
| 6,595,975 B2 | 7/2003 | Vogt et al. | |
| 6,605,172 B1 | 8/2003 | Anderson et al. | |
| 6,616,648 B2 | 9/2003 | Hermansson et al. | |
| 6,623,468 B2 | 9/2003 | Shimoe | |
| 6,623,837 B2 | 9/2003 | Morman et al. | |
| 6,627,564 B1 | 9/2003 | Morman et al. | |
| 6,632,211 B2 | 10/2003 | Otsubo | |
| 6,641,568 B2 | 11/2003 | Ashton et al. | |
| 6,667,258 B2 | 12/2003 | Quinn | |
| 6,677,258 B2 | 1/2004 | Carroll et al. | |
| 6,680,265 B1 | 1/2004 | Smith et al. | |
| 6,680,422 B2 | 1/2004 | Roe | |
| 6,717,028 B1 | 4/2004 | Oberstadt | |
| 6,726,792 B1 | 4/2004 | Johnson et al. | |
| 6,746,434 B2 | 6/2004 | Johnson et al. | |
| 6,811,865 B2 | 11/2004 | Morman et al. | |
| 6,811,871 B2 | 11/2004 | Sen et al. | |
| 6,827,806 B2 | 12/2004 | Uitenbroek et al. | |
| 6,843,134 B2 | 1/2005 | Anderson et al. | |
| 6,849,324 B2 | 2/2005 | Meece et al. | |
| 6,875,710 B2 | 4/2005 | Eaton et al. | |
| 6,896,843 B2 | 5/2005 | Topolkaraev et al. | |
| 6,909,028 B1 | 6/2005 | Shawver et al. | |
| 6,915,700 B2 | 7/2005 | Anderson et al. | |
| 6,942,894 B2 | 9/2005 | Alberg et al. | |
| 7,013,941 B2 | 3/2006 | Schneider et al. | |
| 7,024,939 B2 | 4/2006 | Anderson et al. | |
| 7,028,735 B2 | 4/2006 | Schneider et al. | |
| 7,056,411 B2 | 6/2006 | Desai et al. | |
| 7,062,983 B2 | 6/2006 | Anderson et al. | |
| 7,066,921 B2 | 6/2006 | Schmoker et al. | |
| 7,087,287 B2 | 8/2006 | Curro et al. | |
| 7,094,227 B2 | 8/2006 | Ishiguro et al. | |
| 7,122,022 B2 | 10/2006 | Drevik | |
| 7,223,818 B2 | 5/2007 | Autran et al. | |
| 7,744,579 B2 | 6/2010 | Langdon et al. | |
| 1,155,659 A1 | 7/2010 | Johnson | |
| 2001/0023341 A1 | 9/2001 | Karami | |
| 2001/0041879 A1 | 11/2001 | Karami et al. | |
| 2001/0042584 A1 | 11/2001 | Karami et al. | |
| 2002/0002021 A1 | 1/2002 | May et al. | |
| 2002/0007164 A1 | 1/2002 | Boggs et al. | |
| 2002/0010455 A1 | 1/2002 | Hermansson et al. | |
| 2002/0035354 A1 | 3/2002 | Mirle et al. | |
| 2002/0045879 A1 | 4/2002 | Karami | |
| 2002/0111598 A1 | 8/2002 | Vogt et al. | |
| 2002/0138065 A1 | 9/2002 | Yeater | |
| 2002/0151858 A1 | 10/2002 | Karami et al. | |
| 2003/0021951 A1 | 1/2003 | Desai et al. | |
| 2003/0065298 A1 | 4/2003 | Mirle et al. | |
| 2003/0078558 A1 | 4/2003 | Karami et al. | |
| 2003/0084996 A1 | 5/2003 | Alberg et al. | |
| 2003/0087059 A1 | 5/2003 | Jackson et al. | |
| 2003/0087098 A1 | 5/2003 | Eaton et al. | |
| 2003/0088220 A1 | 5/2003 | Molander et al. | |
| 2003/0088228 A1 | 5/2003 | Desai et al. | |
| 2003/0091807 A1 | 5/2003 | Desai et al. | |
| 2003/0109842 A1 | 6/2003 | Louis et al. | |
| 2003/0144645 A1 | 7/2003 | Karami | |
| 2003/0162458 A1 | 8/2003 | Tsujiyama et al. | |
| 2003/0220626 A1 | 11/2003 | Karami | |
| 2003/0225382 A1 | 12/2003 | Tombult-Meyer et al. | |
| 2003/0233082 A1 | 12/2003 | Kline et al. | |
| 2004/0006326 A1 | 1/2004 | Nakajima et al. | |
| 2004/0024109 A1 | 2/2004 | Hamersky et al. | |
| 2004/0049836 A1 | 3/2004 | Ashraf et al. | |
| 2004/0082933 A1 | 4/2004 | Karami | |
| 2004/0092677 A1 | 5/2004 | Hanke et al. | |
| 2004/0110442 A1 | 6/2004 | Rhim et al. | |
| 2004/0121687 A1 | 6/2004 | Morman et al. | |
| 2004/0121690 A1 | 6/2004 | Mleziva | |
| 2004/0132374 A1 | 7/2004 | Kobayashi | |
| 2004/0153043 A1 | 8/2004 | Sugito et al. | |
| 2004/0162536 A1 | 8/2004 | Becker et al. | |
| 2004/0167486 A1 | 8/2004 | Busam et al. | |
| 2004/0173036 A1 | 9/2004 | Anderson et al. | |
| 2004/0193133 A1 | 9/2004 | Desai et al. | |
| 2004/0193134 A1 | 9/2004 | Mueller et al. | |
| 2004/0222553 A1 | 11/2004 | Desai et al. | |
| 2004/0224132 A1 * | 11/2004 | Roe et al. | 428/175 |

(56) References Cited

U.S. PATENT DOCUMENTS

| | | |
|---|---|---|
| 2005/0070866 A1 | 3/2005 | Isele et al. |
| 2005/0096624 A1 | 5/2005 | Hoshino et al. |
| 2005/0106980 A1 | 5/2005 | Abed et al. |
| 2005/0124952 A1 | 6/2005 | Zehner et al. |
| 2005/0130544 A1 | 6/2005 | Cheng et al. |
| 2005/0154366 A1 | 7/2005 | Karami et al. |
| 2005/0164586 A1 | 7/2005 | Autran et al. |
| 2005/0165173 A1 | 7/2005 | Autran et al. |
| 2005/0177123 A1 | 8/2005 | Catalan |
| 2005/0211368 A1 | 9/2005 | McGuire et al. |
| 2005/0214461 A1 | 9/2005 | Desai et al. |
| 2005/0215963 A1 | 9/2005 | Autran et al. |
| 2005/0215964 A1 | 9/2005 | Autran et al. |
| 2005/0215972 A1 | 9/2005 | Roe et al. |
| 2005/0215973 A1 | 9/2005 | Roe et al. |
| 2005/0256476 A1 | 11/2005 | Mirle et al. |
| 2005/0273072 A1* | 12/2005 | Hird et al. ............... 604/385.24 |
| 2006/0014460 A1 | 1/2006 | Isele et al. |
| 2006/0129119 A1 | 6/2006 | Kistler |
| 2006/0141883 A1 | 6/2006 | Nishiguchi et al. |
| 2006/0155253 A1 | 7/2006 | Dziezok et al. |
| 2006/0155254 A1 | 7/2006 | Sanz et al. |
| 2006/0189956 A1 | 8/2006 | Catalan |
| 2007/0078427 A1 | 4/2007 | Raycheck et al. |
| 2007/0093769 A1 | 4/2007 | Kline et al. |
| 2007/0142815 A1 | 6/2007 | Macura et al. |
| 2007/0202767 A1 | 8/2007 | Anderson et al. |
| 2007/0287348 A1 | 12/2007 | Autran et al. |
| 2007/0287981 A1 | 12/2007 | Roe et al. |
| 2007/0287982 A1 | 12/2007 | Lodge et al. |
| 2007/0287983 A1 | 12/2007 | Lodge et al. |
| 2008/0004582 A1 | 1/2008 | Lodge et al. |
| 2008/0004583 A1 | 1/2008 | Desai et al. |
| 2008/0004584 A1 | 1/2008 | Langdon et al. |
| 2008/0004586 A1 | 1/2008 | Lodge et al. |
| 2008/0004587 A1 | 1/2008 | Lodge et al. |
| 2008/0004589 A1 | 1/2008 | Roe et al. |
| 2008/0004590 A1 | 1/2008 | Lodge et al. |
| 2008/0004591 A1 | 1/2008 | Desai et al. |
| 2008/0004592 A1 | 1/2008 | Lodge et al. |
| 2008/0004593 A1 | 1/2008 | Lodge et al. |
| 2008/0015537 A1 | 1/2008 | Lodge et al. |
| 2008/0045917 A1 | 2/2008 | Autran |
| 2008/0114326 A1 | 5/2008 | Roe et al. |
| 2008/0125739 A1 | 5/2008 | Lodge et al. |
| 2008/0188822 A1 | 8/2008 | Lodge et al. |

FOREIGN PATENT DOCUMENTS

| | | |
|---|---|---|
| EP | 1 350 493 A1 | 10/2003 |
| EP | 1 787 610 | 5/2007 |
| GB | 243 719 | 2/1926 |
| WO | WO 95/16746 A1 | 6/1995 |
| WO | WO9516746 A1 | 6/1995 |
| WO | WO 96/35402 A1 | 11/1996 |
| WO | WO 98/48750 | 11/1998 |
| WO | WO 03039421 A | 5/2003 |
| WO | WO2005065680 A1 | 7/2005 |
| WO | WO2006017518 A2 | 2/2006 |
| WO | WO2006017674 A1 | 2/2006 |
| WO | WO2006017518 A3 | 12/2006 |

* cited by examiner

Fig. 3D

| Fig. 3D-A | Fig. 3D-B |
|---|---|
| Fig. 3D-C | Fig. 3D-D |
| Fig. 3D-E | Fig. 3D-F |

Fig. 3D-A

|  | C1 | C2 | C3 | C4 | C5 | C6 | C7 | C8 | C9 | C10 | C11 | C12 | C13 |
|---|---|---|---|---|---|---|---|---|---|---|---|---|---|
| R1 | 1.58 | 1.08 | 0.64 | 0.48 | 0.44 | 0.40 | 0.51 | 0.60 | 0.97 | 2.25 | 1.59 | 0.83 | 0.68 |
| R2 | 1.59 | 1.13 | 0.77 | 0.48 | 0.49 | 0.47 | 0.55 | 0.59 | 1.21 | 3.15 | 2.37 | 0.92 | 0.70 |
| R3 | 1.59 | 1.14 | 0.73 | 0.52 | 0.52 | 0.45 | 0.59 | 0.67 | 1.19 | 3.23 | 2.73 | 1.20 | 0.76 |
| R4 | 1.59 | 1.08 | 0.78 | 0.58 | 0.52 | 0.52 | 0.58 | 0.73 | 1.23 | 3.73 | 2.48 | 1.15 | 0.73 |
| R5 | 1.32 | 1.21 | 0.81 | 0.62 | 0.50 | 0.45 | 0.54 | 0.69 | 1.32 | 3.21 | 2.84 | 1.17 | 0.77 |
| R6 | 1.17 | 1.18 | 0.75 | 0.63 | 0.56 | 0.54 | 0.52 | 0.72 | 1.25 | 3.01 | 2.50 | 1.17 | 0.81 |
| R7 | 1.54 | 1.19 | 0.77 | 0.51 | 0.55 | 0.52 | 0.43 | 0.80 | 1.01 | 3.02 | 2.66 | 1.18 | 0.82 |
| R8 | 1.59 | 1.21 | 0.80 | 0.49 | 0.57 | 0.45 | 0.59 | 0.82 | 1.58 | 2.93 | 2.51 | 1.25 | 0.83 |
| R9 | 1.58 | 1.21 | 0.84 | 0.47 | 0.55 | 0.52 | 0.59 | 0.79 | 1.39 | 3.36 | 2.72 | 1.11 | 0.89 |
| R10 | 1.61 | 1.32 | 0.79 | 0.60 | 0.44 | 0.54 | 0.58 | 0.87 | 1.15 | 3.25 | 3.09 | 1.29 | 0.89 |

Fig. 3D-B

|  | C14 | C15 | C16 | C17 | C18 | C19 | C20 | C21 |
|---|---|---|---|---|---|---|---|---|
| R1 | 0.51 | 0.47 | 0.42 | 0.57 | 0.70 | 0.59 | 1.22 | 1.13 |
| R2 | 0.44 | 0.55 | 0.40 | 0.57 | 0.79 | 1.05 | 1.51 | 1.28 |
| R3 | 0.56 | 0.56 | 0.51 | 0.48 | 0.84 | 1.00 | 1.52 | 1.41 |
| R4 | 0.63 | 0.44 | 0.49 | 0.57 | 0.75 | 1.04 | 1.64 | 1.23 |
| R5 | 0.66 | 0.53 | 0.54 | 0.49 | 0.84 | 1.09 | 1.63 | 1.32 |
| R6 | 0.61 | 0.57 | 0.53 | 0.44 | 0.82 | 1.04 | 1.74 | 1.68 |
| R7 | 0.66 | 0.52 | 0.49 | 0.47 | 0.89 | 0.90 | 1.55 | 1.61 |
| R8 | 0.59 | 0.54 | 0.47 | 0.54 | 0.79 | 1.04 | 1.58 | 1.50 |
| R9 | 0.62 | 0.48 | 0.46 | 0.59 | 0.76 | 1.01 | 1.48 | 1.64 |
| R10 | 0.66 | 0.45 | 0.52 | 0.52 | 0.79 | 0.98 | 1.34 | 1.58 |

Fig. 3D-C

|  | C1 | C2 | C3 | C4 | C5 | C6 | C7 | C8 | C9 | C10 | C11 | C12 | C13 |
|---|---|---|---|---|---|---|---|---|---|---|---|---|---|
| R11 | 1.63 | 1.41 | 0.87 | 0.40 | 0.42 | 0.51 | 0.72 | 0.88 | 1.16 | 3.81 | 3.21 | 1.02 | 0.97 |
| R12 | 1.62 | 1.45 | 0.82 | 0.54 | 0.55 | 0.53 | 0.94 | 0.99 | 1.15 | 3.46 | 3.30 | 1.29 | 0.92 |
| R13 | 1.59 | 1.07 | 0.81 | 0.53 | 0.58 | 0.60 | 0.87 | 0.96 | 1.15 | 3.24 | 2.65 | 1.30 | 0.62 |
| R14 | 1.60 | 1.35 | 0.84 | 0.65 | 0.58 | 0.62 | 0.61 | 0.77 | 0.92 | 2.83 | 2.58 | 1.40 | 0.85 |
| R15 | 1.65 | 1.30 | 0.80 | 0.66 | 0.58 | 0.69 | 0.58 | 0.85 | 0.93 | 2.54 | 2.66 | 1.28 | 0.57 |
| R16 | 1.69 | 1.31 | 0.94 | 0.68 | 0.65 | 0.57 | 0.59 | 0.55 | 0.80 | 3.37 | 2.68 | 1.11 | 0.71 |
| R17 | 1.72 | 1.42 | 0.88 | 0.62 | 0.63 | 0.56 | 0.58 | 0.56 | 1.02 | 3.31 | 3.08 | 1.19 | 0.65 |
| R18 | 1.77 | 1.78 | 1.21 | 0.62 | 0.58 | 0.45 | 0.44 | 0.55 | 0.93 | 2.97 | 2.72 | 1.10 | 0.48 |
| R19 | 1.56 | 1.67 | 1.15 | 0.66 | 0.46 | 0.37 | 0.43 | 0.57 | 0.68 | 2.04 | 1.54 | 1.09 | 0.47 |
| R20 | 1.51 | 1.16 | 0.78 | 0.65 | 0.42 | 0.41 | 0.30 |  |  |  |  |  |  |
| R21 | 1.61 | 1.22 | 0.80 | 0.49 | 0.37 | 0.41 |  |  |  |  |  |  |  |

Fig. 3D-D

| | C14 | C15 | C16 | C17 | C18 | C19 | C20 | C21 |
|---|---|---|---|---|---|---|---|---|
| R11 | 0.63 | 0.47 | 0.46 | 0.54 | 0.76 | 1.06 | 1.52 | 1.83 |
| R12 | 0.85 | 0.59 | 0.46 | 0.52 | 0.80 | 0.86 | 1.43 | 1.83 |
| R13 | 0.74 | 0.67 | 0.45 | 0.49 | 0.67 | 1.07 | 1.49 | 1.67 |
| R14 | 0.80 | 0.62 | 0.42 | 0.53 | 0.62 | 1.01 | 1.36 | 1.76 |
| R15 | 0.67 | 0.60 | 0.67 | 0.60 | 0.66 | 0.95 | 1.35 | 1.77 |
| R16 | 0.61 | 0.58 | 0.66 | 0.62 | 0.59 | 0.96 | 1.45 | 1.44 |
| R17 | 0.57 | 0.58 | 0.65 | 0.63 | 0.56 | 1.04 | 1.41 | 1.38 |
| R18 | 0.44 | 0.55 | 0.50 | 0.62 | 1.06 | 1.14 | 1.32 | 1.46 |
| R19 | 0.50 | 0.44 | 0.47 | 0.53 | 1.33 | 1.12 | 1.61 | 1.50 |
| R20 | | 0.50 | 0.44 | 0.48 | 0.79 | 1.09 | 1.39 | 1.58 |
| R21 | | | 0.40 | 0.47 | 0.60 | 0.94 | 1.34 | 1.22 |

Fig. 3D-E

|     | C1   | C2   | C3   | C4   | C5   | C6 | C7 | C8 | C9 | C10 | C11 | C12 | C13 |
|-----|------|------|------|------|------|----|----|----|----|-----|-----|-----|-----|
| R22 | 1.52 | 1.32 | 0.77 | 0.57 | 0.20 |    |    |    |    |     |     |     |     |
| R23 | 1.57 | 1.48 | 0.82 | 0.39 |      |    |    |    |    |     |     |     |     |
| R24 | 1.20 | 0.86 | 0.59 |      |      |    |    |    |    |     |     |     |     |

Fig. 3D-F

|     | C14 | C15 | C16  | C17  | C18  | C19  | C20  | C21  |
|-----|-----|-----|------|------|------|------|------|------|
| R22 |     |     | 0.35 | 0.47 | 0.36 | 0.94 | 1.38 | 1.23 |
| R23 |     |     |      |      |      |      |      |      |
| R24 |     |     |      |      |      |      |      |      |

DISPOSABLE WEARABLE ABSORBENT ARTICLES WITH ANCHORING SUBSYSTEMS

CROSS REFERENCE TO RELATED APPLICATIONS

This application is a continuation in part of U.S. application Ser. No. 11/899,812, filed Sep. 7, 2007, which is hereby incorporated by reference, and this application claims the benefit of that prior application.

FIELD

In general, embodiments of the present disclosure relate to wearable absorbent articles. In particular, embodiments of the present disclosure relate to disposable wearable absorbent articles with anchoring subsystems.

BACKGROUND

Disposable wearable absorbent articles include disposable diapers and disposable incontinence undergarments. A disposable wearable absorbent article can receive and contain bodily waste while being worn by a wearer. Such articles can be made with various materials in a number of configurations. The design of a disposable wearable absorbent article can affect the way that the article fits on a wearer. Unfortunately, some disposable wearable absorbent articles fit wearers poorly. As an example, some disposable wearable absorbent articles can sag or slip down on a wearer. A disposable wearable absorbent article that sags or slips down on a wearer can feel uncomfortable, look unattractive, and perform poorly as the article tends to leak.

BRIEF DESCRIPTION OF THE DRAWINGS

FIG. 3D illustrates an exemplary chart with modulus of elasticity values, obtained from the modulus mapping method testing and recorded for each square of the map of the embodiment of FIG. 3A, according to embodiments of the present disclosure.

DETAILED DESCRIPTION

Figure 1A:
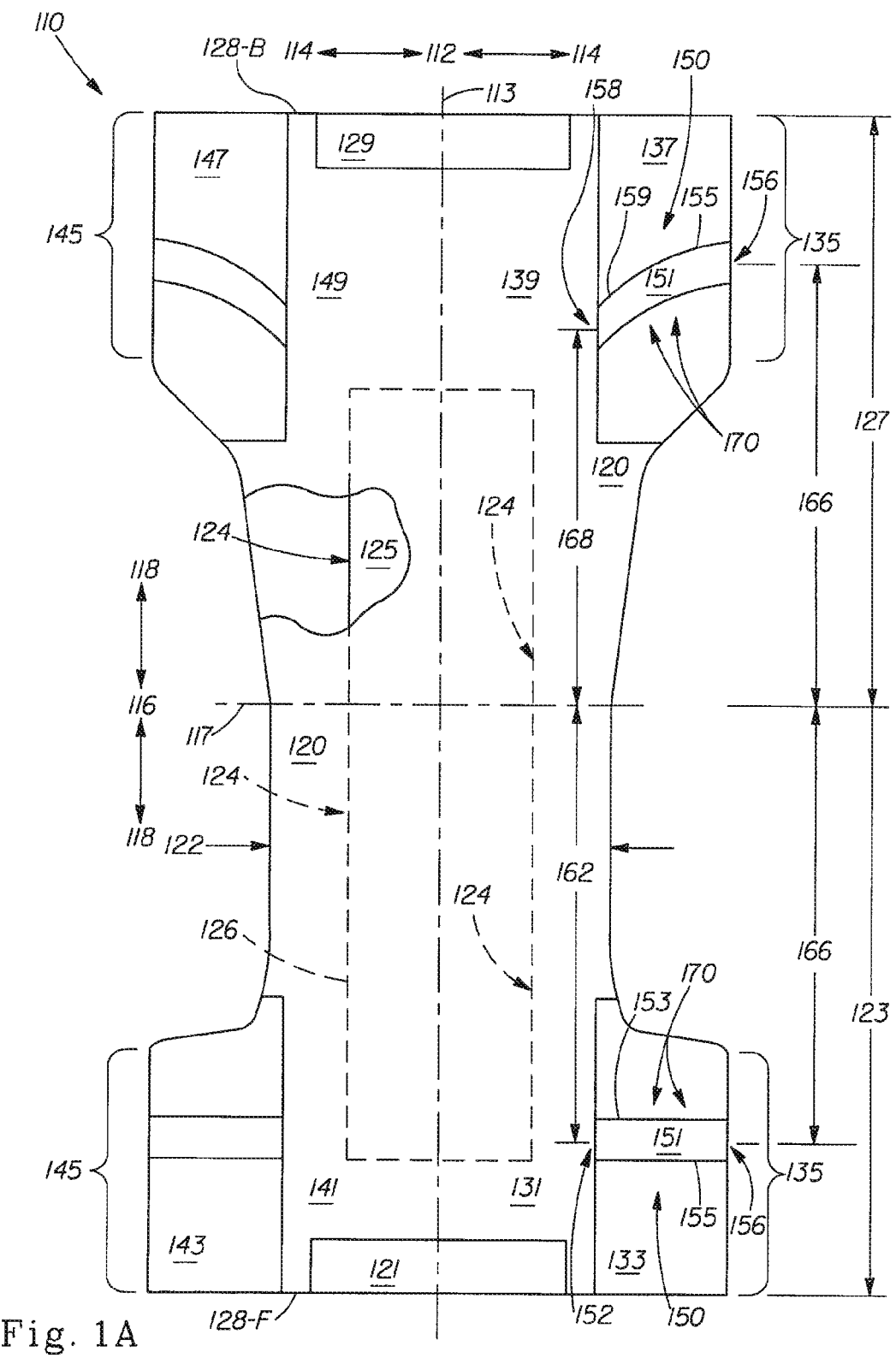
FIG. 1A illustrates a plan view of an inside of a pant-type disposable wearable absorbent article including a side panel with an anchoring subsystem having exactly one side anchoring member, according to embodiments of the present disclosure.

Embodiments of the present disclosure include disposable wearable absorbent articles with anchoring subsystems that fit wearers well. The designs of these articles help prevent the articles from sagging or slipping down on a wearer. As a result, the disposable wearable absorbent articles of the present disclosure can feel comfortable, look attractive, and perform well as the articles tend to stay in place on wearers and not leak.

Embodiments of the present disclosure include disposable wearable absorbent articles. Throughout the present disclosure, the term "disposable wearable absorbent article" refers to an article, configured to be worn on a lower torso of a human body of a wearer, configured to receive and contain bodily exudates (e.g., urine and feces) from the body, and configured to be partly or wholly disposed of after a single use by the wearer. Thus, a disposable wearable absorbent article is configured such that the soiled article, or a soiled portion of the article, is not intended to be restored and reused (e.g., not intended to be laundered). Examples of disposable wearable absorbent articles include disposable diapers, disposable incontinence undergarments, etc. A disposable wearable absorbent article can be configured in various ways, such as a pant-type configuration or a front fastenable configuration.

In embodiments of the present disclosure, a disposable wearable absorbent article can include an absorbent core. Throughout the present disclosure, the term "absorbent core" refers to a part of a disposable wearable absorbent article configured to absorb bodily exudates received into the article from a body of a wearer. An absorbent core can be configured in various ways, as will be understood by one of ordinary skill in the art. Examples of absorbent cores include absorbent core assemblies (with one or more optional core structures), bucket-shaped absorbent cores, removable and/or replaceable absorbent cores, etc.

When a disposable wearable absorbent article is placed on a wearer, the article is placed in an initial position with respect to the wearer. The location of this initial position can depend on a number of factors, such as the size of the article, the shape of the wearer's body, and the manner in which the article is placed on the wearer. For example, an initial position of a fastenable diaper can depend in part on a location at which the diaper is fastened around a wearer. However, as a disposable wearable absorbent article is worn by a wearer, a number of forces can act upon the article.

Some of these forces can tend to move the article on the wearer. Throughout the present disclosure, the term "load" refers to a force that tends to move a disposable wearable absorbent article out of place on a wearer. First, a disposable wearable absorbent article can experience various loads from placement of the article on a wearer. As an example, some pretension forces from fastening the article can drive the article downward. Second, a disposable wearable absorbent article can experience various loads from the article's environment. A wearer's clothes can pull on the article, for example. Third, a disposable wearable absorbent article can experience various loads from a wearer's movements. For example, as a wearer changes positions or moves about, the wearer's body can push against parts of the article or create dynamic forces in the article. Fourth, the force of gravity can move a disposable wearable absorbent article down on a wearer. The article can experience a significant load from the force of gravity, due to a mass of the article as well as a mass of any bodily waste contained by the article. These loads, can act upon a disposable wearable absorbent article, tending to move the article on a wearer.

However, other forces acting upon a disposable wearable absorbent article can tend to hold the article in place on a wearer. First, a disposable wearable absorbent article can experience various holding forces from placement of the article on a wearer. As an example, other pretension forces from fastening the article can drive the article upward. Second, parts of a disposable wearable absorbent article can experience friction forces from contact with a wearer's skin. For example, the article can experience a friction force where a waistband of the article wraps around and against the wearer's waist. Third, parts of a disposable wearable absorbent article can experience reaction forces from contact with various external anatomical features on a wearer's body. As an example, the article can experience reaction forces where the article contacts protruding portions of the wearer's hips. In this example, the reaction forces react against the force of gravity by pushing up on the article. These holding forces can act upon a disposable wearable absorbent article, tending to hold the article in place on a wearer.

As some forces tend to move a disposable wearable absorbent article down on a wearer and other forces tend to hold the article up on the wearer, part or all of the article may or may not move, depending on whether or not such forces are balanced. If the forces tending to hold the article up can equal the forces tending to move the article down, then the article can hold in place on the wearer. If the forces tending to move the article down are greater than the forces tending to hold the article up, then part or all of the article can move out of place and down on the wearer. Sometimes, forces can move down part or all of disposable wearable absorbent article, resulting in sagging and/or slipping.

However, embodiments of the present disclosure can help prevent disposable wearable absorbent articles from sagging and/or slipping down on a wearer. A disposable wearable absorbent article can include an anchoring subsystem. In various embodiments, an anchoring subsystem can be configured to collect at least some of the loads acting upon the article. The anchoring subsystem can also be configured to anchor itself to a body of a wearer. In this way, the anchoring subsystem can balance at least some of the collected loads with holding forces obtained from the anchoring. By balancing the collected loads with the obtained holding forces, the anchoring subsystem can at least assist in holding the disposable wearable absorbent article in place on a wearer.

An anchoring subsystem can be configured to collect loads acting upon a disposable wearable absorbent article, to anchor itself to a body of a wearer, and to balance the collected loads with holding forces obtained from the anchoring. Throughout the present disclosure, the term "anchored" refers to a configured relationship between part or all of an anchoring subsystem in a disposable wearable absorbent article and part or all of a body of a wearer, while the article is worn by the wearer. Where an element of an anchoring subsystem is anchored to a portion of a body of a wearer, at least part of the element is in direct and/or indirect contact with the portion of the body and the anchoring subsystem is configured to at least reduce and/or prevent relative movement between the element and the portion, while the article is worn by the wearer.

An anchoring subsystem can be anchored to a body of a wearer with one or more elements of the anchoring subsystem configured to contact various parts of a body of a wearer. For example, an anchoring subsystem can be at least partially anchored by wrapping one or more anchoring subsystem elements at least partway around a front, back, and/or side of a body of a wearer, thus creating friction and/or reaction forces.

A part of the body with a relatively smaller radius of curvature can, in some embodiments, provide greater friction forces, since an element can tend to wrap around such parts more tightly. This is due to the physics of a flexible material that is wrapped around a curved surface and placed under tension. In this scenario, as a tensile force places the flexible material under tension, the flexible material exerts a normal force perpendicular to and inward on the curved surface. According to the basic Capstan formula, the normal force is proportional to the tensile force divided by the radius of the curved surface. Thus, at a given tensile force as the radius becomes smaller the normal force becomes larger.

Also as an example, an anchoring subsystem can be at least partially anchored by setting one or more anchoring subsystem elements on, around, and/or above protruding portions of a body of a wearer, thus creating friction and/or reaction forces. A part of the body with a relatively larger horizontal protrusion can, in some embodiments, provide greater reaction forces, since an element can tend to hang and/or ride on such parts more securely.

In order to collect loads, anchor itself to a body of a wearer, and balance various forces, an anchoring subsystem can be configured to include one or more anchoring subsystem elements. In some embodiments, an anchoring subsystem element can be an elongated element configured to carry tension. Anchoring subsystem elements can follow various pathways on external surfaces of a body of a wearer of the disposable wearable absorbent article in which the anchoring subsystem is included. The shapes of these external surfaces can affect the shapes of the pathways. The shapes of the pathways can, in turn, affect configurations of anchoring subsystem elements.

Many external surfaces on human bodies include curved shapes, such as a curve around a hip of a human body. Different human bodies can include different curves as bodies have various sizes and shapes. In some embodiments, part or all of an anchoring subsystem element that follows a curved pathway can be a geodesic.

The term geodesic relates to a theoretical element with mathematical properties described by curved geometries. In this theoretical context, a geodesic is a curved line on a curved surface, wherein the curved line appears to travel straight, without turning to the left or to the right, when viewed from that curved surface. In other words, a geodesic can be thought of as a line pulled taut on a frictionless curved surface. On a flat surface, the shortest distance between two points is a straight line. On a curved surface, the shortest distance between two points is a geodesic. More information on geodesics and their mathematical properties can be found in texts on differential geometry and the theory of general relativity, for example Barrett O'Neill, Elementary Differential Geometry Ch. 7 (Academic Press 2006); and James Foster & David J. Nightingale, A Short Course in General Relativity Ch. 2.1 (Springer Science and Business Media 2006).

Part or all of an anchoring subsystem element can be configured as a geodesic. While, throughout the present disclosure, anchoring subsystem elements are described as geodesics, these descriptions are intended to mean that such anchoring subsystem elements are configured as close approximations to theoretical geodesic elements. Real world elements cannot behave exactly like theoretical geodesic elements since real world elements always have at least some thickness, always experience at least some friction, and are always subject to at least some small non-axial outside forces, as will be understood by one of ordinary skill in the art.

Part or all of an anchoring subsystem element can be configured as a geodesic as the element follows various convex curved pathways on external surfaces of a body of a wearer. An anchoring subsystem element that is loaded in tension (e.g., axial loading) can be configured as a geodesic, since the tension can conform the element to the convex curved pathway. When a point load is added to an anchoring subsystem element that is a geodesic, at an angle other than in-line with the geodesic, that point load deforms the original geodesic, dividing the original geodesic into two new geodesics in the anchoring subsystem element.

Similarly, when an anchoring subsystem element, configured in tension as a geodesic, passes over a concave portion of a generally convex external surface of a human body, the element bridges the concave portion, separating the anchoring subsystem element into two geodesics on either convex side of the concave portion. Further, the bridging portion of the anchoring subsystem element is also a geodesic, since it is a straight line in space.

When an anchoring subsystem element that is a geodesic is subjected to a load distributed along at least a portion of the length of the element, at an angle other than in-line with the geodesic, the element no longer behaves as a geodesic, and instead begins to act in a manner referred to herein as "geometric anchoring." An anchoring subsystem can include one or more anchoring subsystem elements, at least some of which can be configured as geodesics.

One kind of anchoring subsystem element is a side anchoring member (SAM). A SAM is one or more physical, tension-carrying elements and/or areas disposed along a defined SAM pathway in an anchoring subsystem of a disposable wearable absorbent article. A SAM has two defined ends, a middle between the two ends, and a defined length from its one end to its other end. A SAM can have one or more widths, each of which is less than its defined length. A SAM also has a centerline, running along the SAM pathway, in the center of its width, from its one end to its other end. A SAM pathway cannot substantially or completely encircle the lower torso of the body of the wearer. At least a portion of a SAM pathway passes through a side of the disposable wearable absorbent article. In some embodiments, a SAM can be contained within a side of the disposable wearable absorbent article. Further, in various embodiments, a SAM can be contained within a side panel or a side ear of a disposable wearable absorbent article.

A side of a disposable wearable absorbent article can be defined in various ways. A side of a disposable wearable absorbent article can include a portion of a front of the article as well as a portion of a back of the article. Sometimes, a side of a disposable wearable absorbent article can be considered disposed in a portion of the article that is laterally offset from a longitudinal centerline of the article. Throughout the present disclosure, unless otherwise stated, a side of a disposable wearable absorbent article is disposed in a portion of the article that is laterally outboard from longitudinal edges of an absorbent core of the article. In some instances, a side of a disposable wearable absorbent article can be considered disposed in a portion of the article that is laterally outboard from a narrowest portion of a chassis of the article. In various instances, a side of a disposable wearable absorbent article can be considered disposed in a side panel or a side ear of the article. Embodiments of the present disclosure can be used with any of these definitions of a side of a disposable wearable absorbent article.

In an anchoring subsystem of a disposable wearable absorbent article, one or more SAMs can be configured to contact various parts of a body of a wearer, to at least assist in anchoring the anchoring subsystem to the body. A SAM can receive at least some collected loads from one or more elements of the disposable wearable absorbent article, such as a chassis, a fastener, a leg cuff, etc. A SAM can also provide holding forces to help balance the collected loads through contact with the body. In balancing these loads and forces, the SAM carries tensions in the anchoring system. This balancing can enable the anchoring subsystem to at least assist in holding a disposable wearable absorbent article in place on a wearer.

A SAM can be configured in various forms. In some embodiments, a SAM can include a number of elements, such as fasteners. Part or all of a SAM can be straight, curved, angled, segmented, or other shapes, or combinations of any of these shapes. A SAM pathway can be a unitary, continuous pathway, or can be formed by a number of discrete elements and/or separate areas disposed along a SAM pathway. As examples, a SAM can be formed by substantially parallel strands of material running through a side panel or a side ear, or by a series of pieces of material attached to a side panel or a side ear, or by a distribution of unstretched areas in an incrementally stretched side panel or side ear.

Part or all of a SAM can be structurally associated with one or more elements of the disposable wearable absorbent article. As examples, part or all of a SAM can be discrete from and/or joined to and/or attached to and/or embedded in and/or integral with one or more elements of the disposable wearable absorbent article. Throughout the present disclosure, the term "joined" refers to configurations whereby an element is directly connected to another element by affixing the element directly to the other element and to configurations whereby an element is indirectly secured to another element by affixing the element to intermediate member(s) which in turn are affixed to the other element.

A SAM can be made from any material suitable for carrying tensions in an anchoring system. Part or all of a SAM can include one or more of various elastic, inelastic, extensible, inextensible, stretchable, and/or non-stretchable material(s) and/or any other suitable material(s) and/or combinations of any of these materials. As examples, part or all of a SAM can include one or more of various elastomeric materials, such as extruded films, elastics, nonwovens, scrims, slot-coated films, sprayed or melt-blown fibers, and/or printed elastics and/or any other suitable elastomeric material(s) and/or combinations of any of these materials.

Also as examples, part or all of a SAM can be structurally associated with part or all of one or more elements of a disposable wearable absorbent article, such as embodiments wherein one or more of the element(s) are configured with an elastic nonwoven, with an elastic film and extensible nonwoven, with an extensible film and an elastic nonwoven, to be pre-stretched with elastic strands allowed to contract, to be incrementally stretched, with zero strain laminate, and/or in combinations of these and/or other configurations. In some embodiments, a SAM can include one or more laminate materials. In various embodiments, a SAM can be formed from various basis weights, chemistries, and/or incremental stretchings, as will be understood by one of ordinary skill in the art.

A SAM can be any suitable width or thickness. For example, a SAM can be from 5 mm to about 50 mm wide or any width within that range. The width and/or thickness of a SAM can be substantially or completely uniform over one or more parts of the SAM or over the entire length of the SAM, or can vary over the length of the SAM. In some embodiments, a SAM can have a substantially uniform width of about 10 mm, about 20 mm, or about 30 mm. Throughout the present disclosure, unless otherwise stated, the width of a SAM is measured at a particular point on the SAM's pathway, as the largest overall dimension across the pathway, from one side edge of the pathway to the other side edge of the pathway, in a direction perpendicular to the SAM's centerline.

As described above, an anchoring subsystem can balance loads and forces, thus performing functions similar to those of an anchoring system for a disposable wearable absorbent article, as described in U.S. patent application Ser. No. 11/599,851. As a result, an anchoring subsystem can provide benefits similar to those of an anchoring system for a disposable wearable absorbent article; helping prevent the article from sagging and/or slipping down on a wearer. However, an anchoring subsystem differs from an anchoring system in the extent of its presence within a disposable wearable absorbent article. In an anchoring subsystem of a disposable wearable absorbent article, no element of the anchoring subsystem substantially or completely encircles the lower torso of a wearer when the disposable wearable absorbent article is worn by the wearer. Further, an anchoring subsystem is contained within a particular, defined area of a disposable wearable absorbent article. For example, a side anchoring subsystem of a disposable wearable absorbent article is contained within a side of the disposable wearable absorbent article.

FIG. 1A illustrates a plan view of an inside of a pant-type disposable wearable absorbent article 110, which includes an anchoring subsystem 170 with exactly one side anchoring member 150.

In FIG. 1A, a longitudinal centerline 113 and a lateral centerline 117 provide lines of reference for referring to relative locations of parts of the disposable wearable absorbent article 110. When a first part is nearer to the longitudinal centerline 113 than a second part, the first part can be considered laterally inboard 112 to the second part. Similarly, the second part can be considered laterally outboard 114 from the first part. When a third part is nearer to the lateral centerline 117 than a fourth part, the third part can be considered longitudinally inboard 116 to the fourth part. Similarly, the fourth part can be considered longitudinally outboard 118 from the third part. FIG. 1A includes arrows indicating relative directions for laterally inboard, laterally outboard, longitudinally inboard, and longitudinally outboard, with respect to the disposable wearable absorbent article 110. Throughout the present disclosure, unless otherwise stated, a reference to a longitudinal dimension, measurement, line, or direction refers to a dimension, measurement, line, or direction substantially or completely parallel to the longitudinal centerline 113, and a reference to a lateral dimension, measurement, line, or direction refers to a dimension, measurement, line, or direction substantially or completely parallel to the lateral centerline 117.

The disposable wearable absorbent article 110 includes a front 123 and a back 127. The front 123 is a portion of the disposable wearable absorbent article 110 disposed generally proximate to and/or below the belly of a wearer, when the disposable wearable absorbent article 110 is worn by the wearer. A reference to the "front" can mean the front itself, part or all of an element in the front, and/or a disposition in the front, depending on the context of the reference. The back 127 is a portion of the disposable wearable absorbent article 110 disposed generally proximate to and/or below the back of a wearer, when the disposable wearable absorbent article 110 is worn by the wearer. A reference to the "back" can mean the back itself, part or all of an element in the back, and/or a disposition in the back, depending on the context of the reference. The lateral centerline 117 of the disposable wearable absorbent article 110 forms a boundary between the front 123 and the back 127. The front and back terminology described above is used for disposable wearable absorbent articles throughout the present disclosure, unless otherwise indicated.

The disposable wearable absorbent article 110 also includes a chassis 120, a front waistband 121, a narrowest portion 122 of the chassis 120, an absorbent core 125 with longitudinal edges 124, an absorbent core area 126, a front waist edge 128-F, a back waist edge 128-B, and a back waistband 129. A portion of the chassis 120 is illustrated as cut away in order to show the absorbent core 125 and the longitudinal edges 124 more clearly. A front portion of a first side 131 is disposed in the front 123. A back portion of the first side 139 is disposed in the back 127. The disposable wearable absorbent article 110 has a first side panel, which includes a front portion of the first side panel 133 and a back portion of the first side panel 137, configured to connect via a first side interface 135. Throughout the present disclosure, for clarity, side panels are illustrated as distinct elements within disposable wearable absorbent articles. However, in various embodiments, one or more portions or all of a side panel may not be distinct elements within a disposable wearable absorbent article.

Figure 1B:
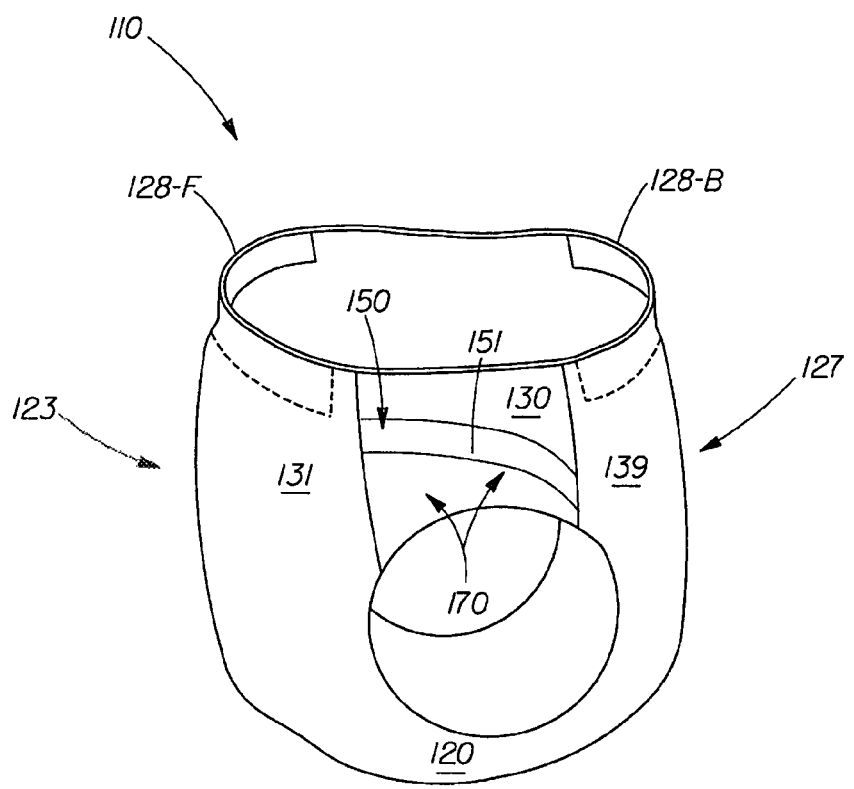
FIG. 1B illustrates a perspective view of an outside of the disposable wearable absorbent article of the embodiment of FIG. 1A, formed for wearing.
Figure 1C:
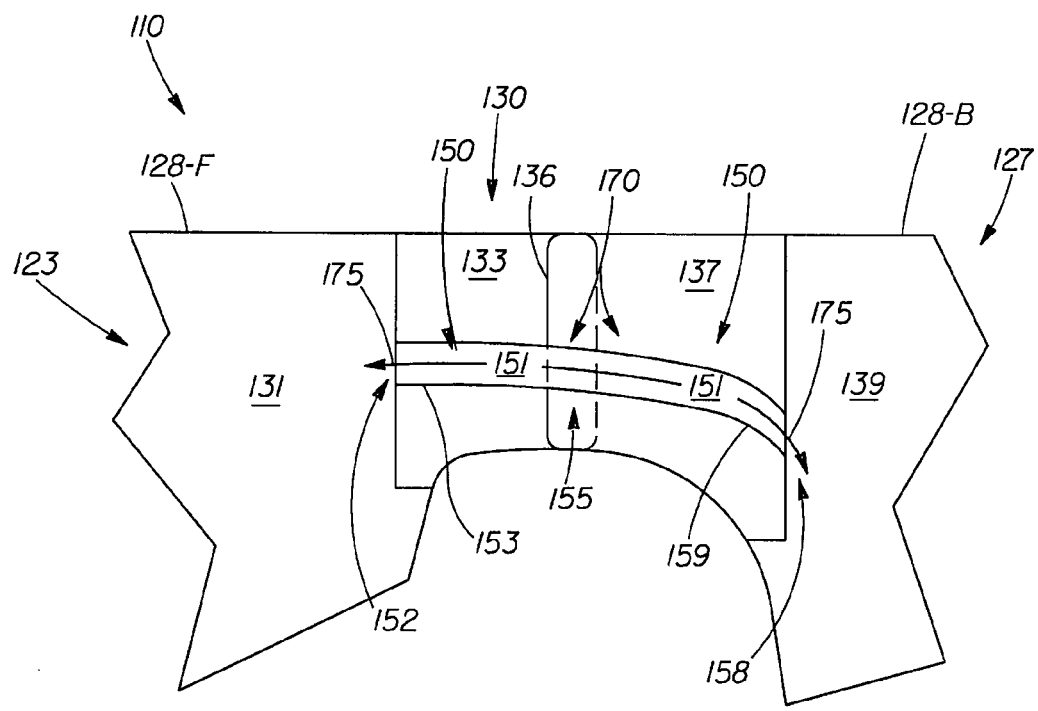
FIG. 1C illustrates an enlarged view of a portion of a side of the disposable wearable absorbent article of the embodiment of FIG. 1B.

The disposable wearable absorbent article 110 includes the anchoring subsystem 170. The anchoring subsystem 170 is not directly connected to the absorbent core 125, and is outside of the absorbent core area 126, so the anchoring subsystem 170 is separate from the absorbent core 125. However, in various embodiments, part or all of one or more elements of an anchoring subsystem can be inside of an absorbent core area, and/or joined or directly connected to an absorbent core. The anchoring subsystem 170 is considered a subsystem because the SAM 150 will not substantially or completely encircle the lower torso of a wearer when the disposable wearable absorbent article 110 is worn. The anchoring subsystem 170 is also considered a subsystem because the anchoring subsystem 170 is contained within a particular, defined portion of the disposable wearable absorbent article 110. In the embodiment of FIGS. 1A-1C, the anchoring subsystem 170 is contained within the first side of the disposable wearable absorbent article 110, so the anchoring subsystem 170 is considered a side anchoring subsystem.

The anchoring subsystem 170 includes the SAM 150. The SAM 150 is considered a side anchoring member because at least a portion of the SAM 150 passes through a side of the disposable wearable absorbent article 110. In the embodiment of FIG. 1A, the SAM 150 is contained within the first side panel. In various embodiments, part or all of the SAM 150 can be configured as a geodesic, so that the anchoring subsystem 170 can provide geodesic anchoring.

For clarity, in the embodiments of FIGS. 1A-3C, SAMs are illustrated as visibly apparent elements. However, in various embodiments, part or all of an anchoring subsystem element may not be readily visibly apparent within a disposable wearable absorbent article. For example, a SAM may not be readily visibly apparent in embodiments wherein the SAM is embedded in or integral with a side panel or a side ear.

The SAM 150 is disposed along a SAM pathway 151. The SAM pathway 151 includes a front end 153, a back end 159, and a middle 155. The front end is disposed in the front 127 at a front end location 152. The back end 159 is disposed in the back 123 at a back end location 158. The middle 155 is disposed along the SAM pathway 151 at a middle location 156 between the front end 153 and the back end 159. In the embodiment of FIG. 1A, the middle location 156 is illustrated as approximately halfway between the front end 153 and the back end 159, bridging the front 123 and the back 129. However, in various embodiments, a middle location can be closer to the front end 153 or closer to the back end 159.

The front end location 152 is located at a front end longitudinally outboard distance 162 from the lateral centerline 117. The back end location 158 is located at a back end longitudinally outboard distance 168 from the lateral centerline 117. The middle location is located at a middle longitudinally outboard distance 166 from the lateral centerline 117.

The back end longitudinally outboard distance 168 is less than the front end longitudinally outboard distance 162 and less than the middle longitudinally outboard distance 166. The front end longitudinally outboard distance 162 is about equal to the middle longitudinally outboard distance 166. In some embodiments, a front end longitudinally outboard distance can be nearly or exactly equal to a middle longitudinally outboard distance. A portion of the SAM pathway 151 between the front end 153 and the middle 155 is oriented laterally while a portion of the SAM pathway 151 between the middle 155 and the back end 159 turns longitudinally inboard as it nears the back end 159.

The front end location 152 is outside of the absorbent core area 126, in the front portion of the first side 131, laterally outboard from the longitudinal edge 124 of the absorbent core 125, within the front portion of the first side panel 133, proximate to a laterally inboard edge of the front portion of the first side panel 133, and laterally inboard to the narrowest portion 122 of the chassis 120. In some embodiments, a front end location can be laterally outboard from the narrowest portion 122 of the chassis 120, and/or outside of the front portion of the first side panel 133, and/or laterally inboard to the longitudinal edges 124 of the absorbent core 125, and/or outside of the front portion of the first side 131.

The back end location 158 is outside of the absorbent core area 126, in the back portion of the first side 139, laterally outboard from the longitudinal edge 124 of the absorbent core 125, within the back portion of the first side panel 137, proximate to a laterally inboard edge of the back portion of the first side panel 137, and laterally inboard to the narrowest portion 122 of the chassis 120. In some embodiments, a back end location can be laterally outboard from the narrowest portion 122 of the chassis 120, and/or outside of the back portion of the first side panel 137, and/or laterally inboard to the longitudinal edges 124 of the absorbent core 125, and/or outside of the back portion of the first side 139.

In the embodiment of FIG. 1A, the front end location 152 and the back end location 158 are both outside of the absorbent core area 126. However, in some embodiments, a front end location can be disposed inside of the absorbent core area while a back end location can be disposed outside of the absorbent core area. In other embodiments, a front end location can be disposed outside of the absorbent core area while a back end location can be disposed inside of the absorbent core area.

The disposable wearable absorbent article 110 also includes a second side with a front portion of the second side 141 disposed in the front 123 and a back portion of the second side 149 disposed in the back 127. The disposable wearable absorbent article 110 has a second side panel, which includes a front portion of the second side panel 143 and a back portion of the second side panel 147, configured to connect via a second side interface 145. In the embodiment of FIG. 1A, the second side panel is configured similar to the first side panel. However, in various embodiments, a second side panel can, alternatively, be configured differently.

The disposable wearable absorbent article 110 can also include an outer cover, which can, in various embodiments, be separate from the anchoring subsystem 170. In some embodiments, part or all of such an outer cover can be stretchable, elastic, or extensible.

FIG. 1B illustrates a perspective view of an outside of the disposable wearable absorbent article 110 of the embodiment of FIG. 1A, formed for wearing. In the embodiment of FIG. 1B, the front portion of the first side panel 133 is connected to the back portion of the first side panel 137 via the first side interface 135 to form the first side panel 130.

FIG. 1C illustrates an enlarged view of a portion of the first side of the disposable wearable absorbent article 110 of the embodiment of FIG. 1B. A connection 136 proximate to the first side interface 135 connects the front portion of the first side panel 133 with the back portion of the first side panel 137 to form the first side panel 130. The connection 136 can take various forms, such as a fastenable connection or a durable connection. The location of the connection 136 can vary in some embodiments. Alternatively, a side can be formed with more than one connection at various locations or without a distinct connection within the side.

In various embodiments of the present disclosure, one or more parts of or at least a portion of the anchoring subsystem 170 can be structurally associated with the first side panel 130. In some embodiments, at least a portion of an anchoring subsystem, or substantially all of an anchoring subsystem, or even all of an anchoring subsystem, can be discrete from, or joined to, or attached to, or embedded in, or integral with a side panel. In various embodiments, at least a portion of the SAM 150, or substantially all of the SAM 150, or even all of the SAM 150, can be discrete from, or joined to, or attached to, or embedded in, or integral with the first side panel 130.

In embodiments in which one or more portions of the anchoring subsystem 170 are integral with the first side panel 130, the first side panel 130 can be considered to have a first portion, which includes the integral portions of the anchoring subsystem 170, and a second portion outside of the first portion. For example, if all of the SAM 150 is integral with the first side panel 130, then the first portion would include the SAM pathway 151, while the second portion would include the area of the first side panel 130 that is longitudinally outboard from the SAM pathway 151 as well as the area of the first side panel 130 that is longitudinally inboard to the SAM pathway 151. In such embodiments, this first portion and second portion can be configured in various ways, as described in the following examples.

The disposable wearable absorbent article 110 can be configured such that substantially all of the first portion can be incrementally stretched to one or more lesser degrees and substantially all of the second portion can be incrementally stretched to one or more greater degrees. The disposable wearable absorbent article 110 can be configured such that the first portion can be incrementally stretched with a first particular number of teeth per a unit of distance, and the second portion can be incrementally stretched with a second particular number of teeth per the unit of distance, wherein the first particular number of teeth can be less than or equal to the second particular number of teeth. As examples, the first particular number of teeth can be at or about nine tenths, or four fifths, or three quarters, or two thirds, or one half, or one third, or one quarter, or one fifth, or one tenth of the second particular number of teeth.

The disposable wearable absorbent article 110 can be configured such that substantially all of the first portion can be configured to have a higher directional modulus of elasticity, and substantially all of the second portion can be configured to have one or more lower directional modulii of elasticity, based on the directionality described in the modulus mapping method described herein. In various embodiments, the higher directional modulus of elasticity can be at least 10, or at least 50, or at least 100, or at least 250, or at least 400 percent greater than the one or more lower directional modulii of elasticity. The disposable wearable absorbent article 110 can be configured such that substantially all of the first portion includes one or more higher caliper elastomers, and substantially all of the second portion includes one or more lower caliper elastomers. The disposable wearable absorbent article 110 can be configured such that substantially all of the first portion includes one or more higher performance elastomers, and substantially all of the second portion includes one or more lower performance elastomers.

The disposable wearable absorbent article 110 can be configured such that one or more unstretched portions can be distributed throughout substantially all of the first portion, and substantially all of the second portion can be incrementally stretched. The disposable wearable absorbent article 110 can be configured such that one or more over-bonded portions can be distributed throughout substantially all of the first portion. The disposable wearable absorbent article 110 can be configured such that substantially all of the first portion can be configured to have one or more higher forces per unit width at a particular strain, and substantially all of the second portion can be configured to have one or more lower forces per unit width at the particular strain. In various embodiments, the ratio of one of the higher force per unit width to one of the lower force per unit width can be at least 1.1, or at least 1.5, or at least 2, or at least 3.5, or at least 5.

In some embodiments, the disposable wearable absorbent article 110 can be configured such that one or more loads in the article can cause tension in the anchoring subsystem 170 before the load can cause tension in a portion of the first side panel that is outside of the anchoring subsystem 170. In various embodiments, the disposable wearable absorbent article 110 can be configured such that one or more loads in the article can cause greater tension in the anchoring subsystem 170 than in a portion of the first side panel that is outside of the anchoring subsystem 170.

In addition to the elements previously described, FIG. 1C also shows tension lines 175. The tension lines 175 illustrate how the SAM 150 can balance collected loads with obtained holding forces, so that the anchoring subsystem 170 can at least assist in holding the disposable wearable absorbent article 110 in place on a wearer. For example, the SAM 150 can collect loads at the front end 153, at the back end 159, and/or along the first SAM pathway 151. As a further example, the SAM 150 can also obtain holding forces the front end 153, at the back end 159, and/or along the first SAM pathway 151 as the SAM 150 experiences anchoring from direct or indirect contact with a wearer's body underneath the first SAM pathway 151.

These loads and forces can be received through various parts of the disposable wearable absorbent article 110, such as the chassis 120 and/or the first side panel 130. The anchoring subsystem 170 is configured to indirectly anchor the absorbent core 125 to a wearer, in that, while the SAM 150 is not directly connected to the absorbent core 125, and the SAM pathway 151 is disposed outside of the absorbent core area 126, loads from the absorbent core 125 can be transmitted through various parts of the disposable wearable absorbent article 110 to the SAM 150, which can balance collected loads with obtained holding forces, so that the anchoring subsystem 170 can at least assist in holding the disposable wearable absorbent article 110 in place on a wearer. As a result, the disposable wearable absorbent article 110 can feel comfortable, look attractive, and perform well as the article tends to stay in place on a wearer and not leak. In addition to the embodiment of FIGS. 1A-1C, a pant-type disposable wearable absorbent article can also include a SAM configured in various other ways, as described in US non-provisional patent applications entitled "Disposable Wearable Absorbent Articles with Anchoring Subsystems" filed on the same date as the present application and further identified by Ser. Nos. 12/204,844, 12/204,854, 12/204,858, and 12/204,864, each of which is incorporated by reference.

Figure 2A:
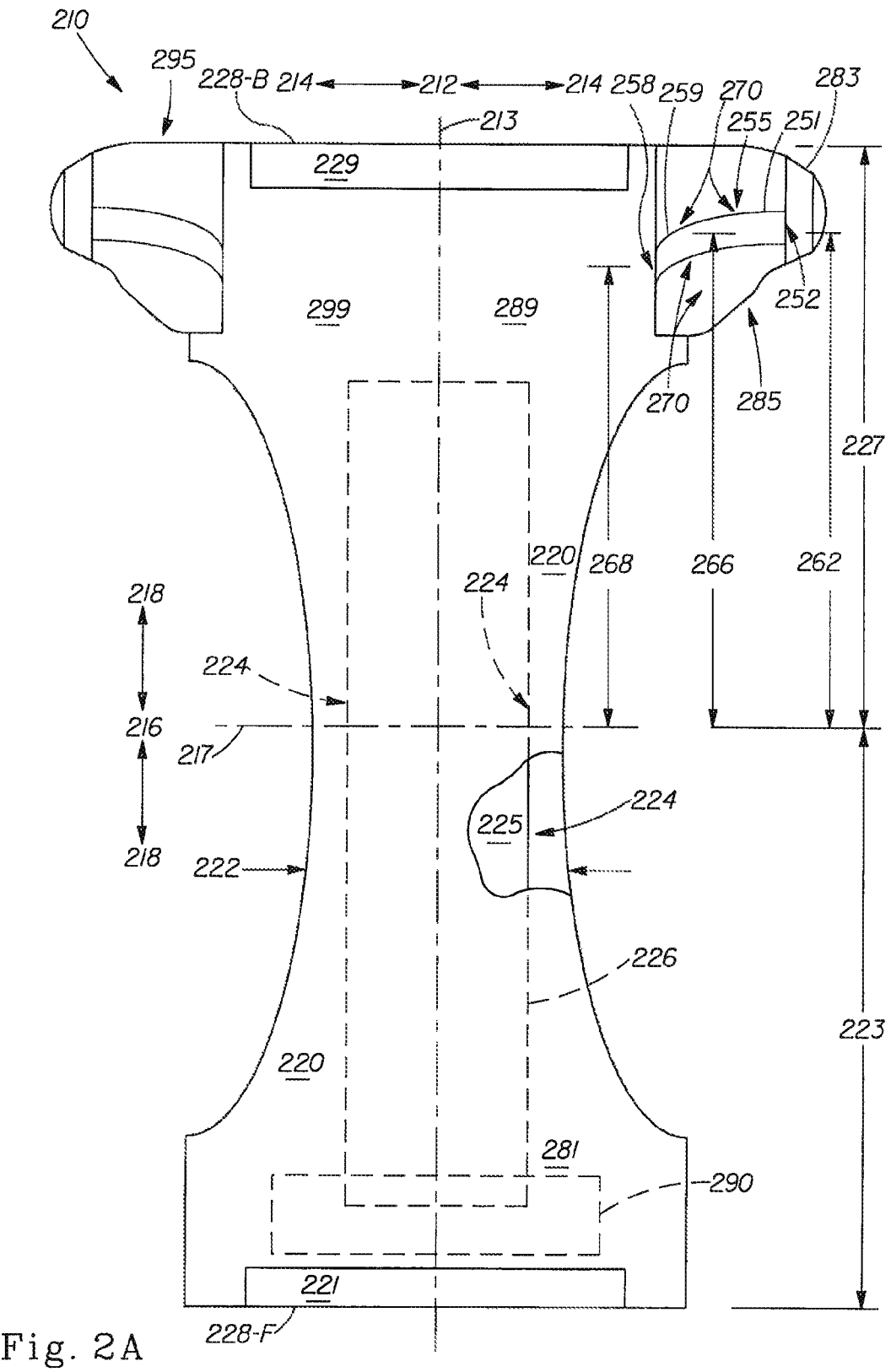
FIG. 2A illustrates a plan view of an inside of a front fastenable disposable wearable absorbent article including a side ear with one fastener as well as an anchoring subsystem having exactly one side anchoring member, according to embodiments of the present disclosure.

FIG. 2A illustrates a plan view of an inside of a front fastenable disposable wearable absorbent article 210, which includes an anchoring subsystem 270 with exactly one side anchoring member 250. A longitudinal centerline 213 and a lateral centerline 217 provide lines of reference for laterally inboard 212, laterally outboard 214, longitudinally inboard 216, and longitudinally outboard 218 relative locations.

The disposable wearable absorbent article 210 includes a front 223 and a back 227. The disposable wearable absorbent article 210 also includes a chassis 220, a front waistband 221, a narrowest portion 222 of the chassis 220, an absorbent core 225 with longitudinal edges 224, an absorbent core area 226, a front waist edge 228-F, a back waist edge 228-B, and a back waistband 229. A portion of the chassis 220 is illustrated as cut away in order to show the absorbent core 225 and the longitudinal edges 224 more clearly. A front portion of a first side 281 is disposed in the front 223. A back portion of the first side 289 is disposed in the back 227.

The disposable wearable absorbent article 210 has a first side ear 285 connected to the back portion of the first side 289. Throughout the present disclosure, for clarity, side ears are illustrated as distinct elements within disposable wearable absorbent articles. However, in various embodiments, one or more portions or all of a side ear may not be distinct elements within a disposable wearable absorbent article. The first side ear 285 includes a fastener 283 disposed proximate to a laterally distal edge of the first side ear 285. The first side ear 285 is configured to fasten to a fastening area 290 in the front 223.

Figure 2B:
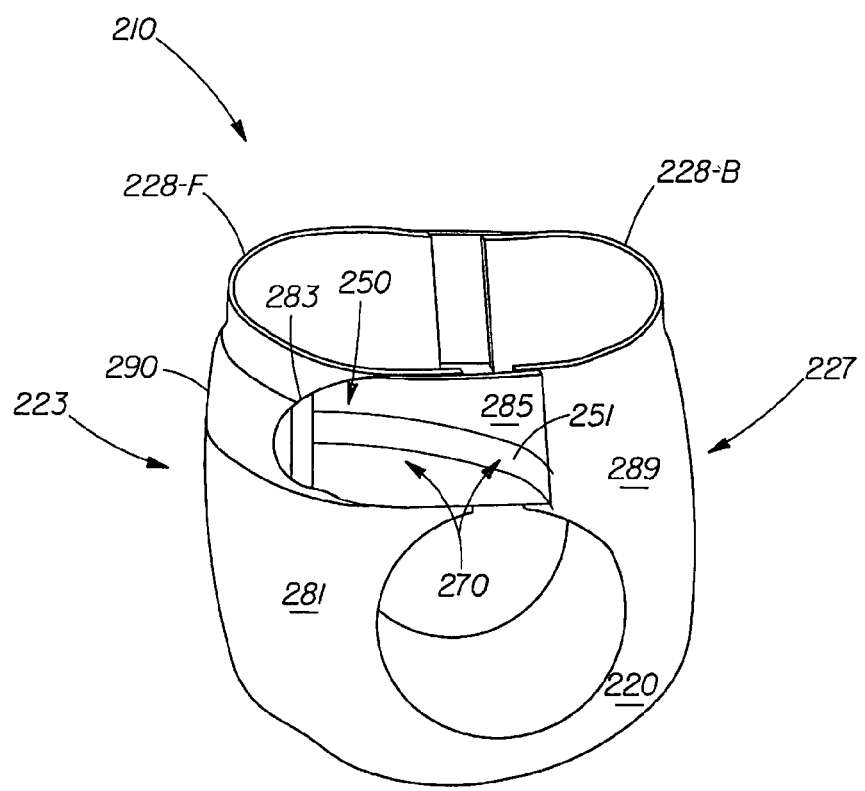
FIG. 2B illustrates a perspective view of an outside of the disposable wearable absorbent article of the embodiment of FIG. 2A, formed for wearing.
Figure 2C:
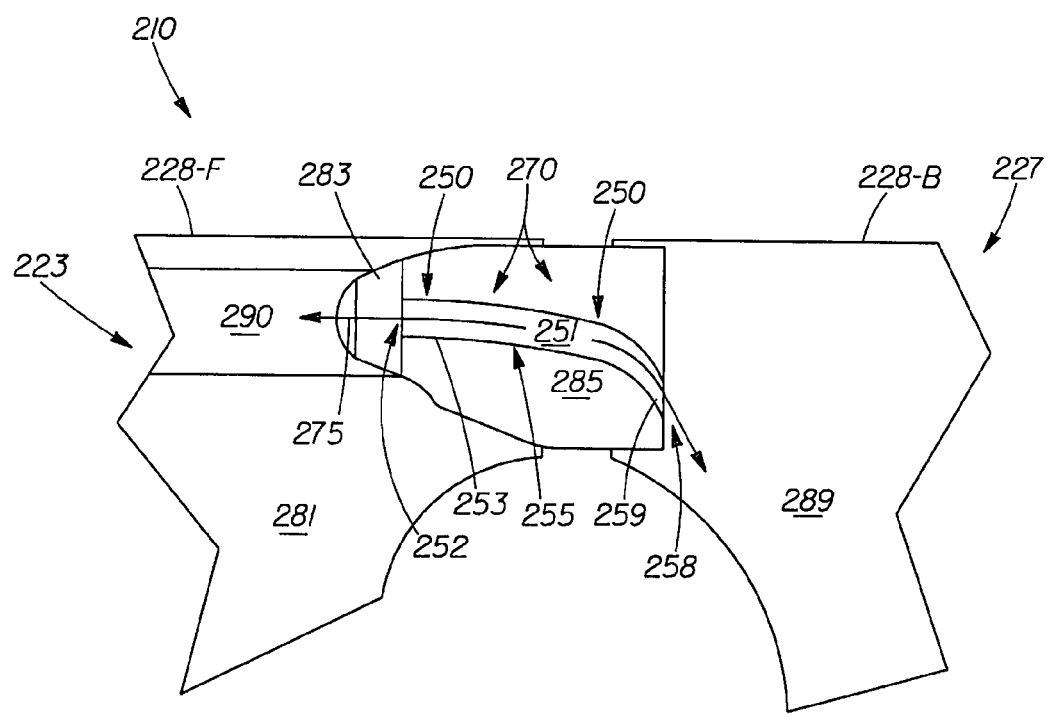
FIG. 2C illustrates an enlarged view of a portion of a side of the disposable wearable absorbent article of the embodiment of FIG. 2B.

The disposable wearable absorbent article 210 includes the anchoring subsystem 270. The anchoring subsystem 270 is not directly connected to the absorbent core 225, and is outside of the absorbent core area 226, so the anchoring subsystem 270 is separate from the absorbent core 225. The anchoring subsystem 270 is considered a subsystem because the SAM 250 will not substantially or completely encircle the lower torso of a wearer when the disposable wearable absorbent article 210 is worn. The anchoring subsystem 270 is also considered a subsystem because the anchoring subsystem 270 is contained within a particular, defined portion of the disposable wearable absorbent article 210. In the embodiment of FIGS. 2A-2C, the anchoring subsystem 270 is contained within the first side of the disposable wearable absorbent article 210, so the anchoring subsystem 270 is considered a side anchoring subsystem.

The anchoring subsystem 270 includes the SAM 250. The SAM 250 is considered a side anchoring member because at least a portion of the SAM 250 passes through a side of the disposable wearable absorbent article 210. In the embodiment of FIG. 2A, the SAM 250 is contained within the first side ear 285. In various embodiments, part or all of the SAM 250 can be configured as a geodesic, so that the anchoring subsystem 270 can provide geodesic anchoring.

The SAM 250 is disposed along a SAM pathway 251. The SAM pathway 251 includes a front end 253, a back end 259, and a middle 255. The front end 253 is disposed at a front end location 252. When the article 210 is laid out flat, as illustrated in FIG. 2A, the front end 253 can be considered disposed in the back 227, since the first side ear 285 is connected to the back portion of the first side 289. However, when the article 210 is formed for wearing, as illustrated in FIG. 2C, the front end 253 can be considered disposed in the front 223, since the first side ear 285 is fastened to the front portion of the first side 281. The back end 259 is disposed at a back end location 258. The middle 255 is disposed along the SAM pathway 251 at a middle location 256 between the front end 253 and the back end 259. In the embodiment of FIG. 2A, the middle location 256 is illustrated as approximately halfway between the front end 253 and the back end 259. However, in various embodiments, a middle location can be closer to the front end 253 or closer to the back end 259.

The front end location 252 is located at a front end longitudinally outboard distance 262 from the lateral centerline 217. The back end location 258 is located at a back end longitudinally outboard distance 268 from the lateral centerline 217. The middle location is located at a middle longitudinally outboard distance 266 from the lateral centerline 217.

The back end longitudinally outboard distance 268 is less than the front end longitudinally outboard distance 262 and less than the middle longitudinally outboard distance 266. The front end longitudinally outboard distance 262 is about equal to the middle longitudinally outboard distance 266. In some embodiments, a front end longitudinally outboard distance can be nearly or exactly equal to a middle longitudinally outboard distance. A portion of the SAM pathway 251 between the front end 253 and the middle 255 is oriented laterally while a portion of the SAM pathway 251 between the middle 255 and the back end 259 turns longitudinally inboard as it nears the back end 259.

The front end location 252 is proximate to the fastener 283. The front end location 252, when the article 210 is formed for wearing, is described in connection with FIG. 2C. The back end location 258 is outside of the absorbent core area 226, in the back portion of the first side 289, laterally outboard from the longitudinal edge 224 of the absorbent core 225, laterally outboard from the narrowest portion 222 of the chassis 220, within the first side ear 285, proximate to a laterally inboard edge of the first side ear 285. In some embodiments, a back end location can be outside of the first side ear 285, and/or laterally inboard to the narrowest portion 222 of the chassis 220, and/or laterally inboard to the longitudinal edges 224 of the absorbent core 225, and/or outside of the back portion of the first side 289, and/or inside of the absorbent core area 226.

The disposable wearable absorbent article 210 also includes a second side with a front portion of the second side 291 disposed in the front 223 and a back portion of the second side 299 disposed in the back 227. The disposable wearable absorbent article 210 has a second side ear 295, configured to fasten to the fastening area 290. In the embodiment of FIG. 2A, the second side ear 295 is configured similar to the first side ear 285. However, in various embodiments, a second side ear can, alternatively, be configured differently.

The disposable wearable absorbent article 210 can also include an outer cover, which can, in various embodiments, be separate from the anchoring subsystem 270. In some embodiments, part or all of such an outer cover can be stretchable, elastic, or extensible.

FIG. 2B illustrates a perspective view of an outside of the disposable wearable absorbent article 210 of the embodiment of FIG. 2A, formed for wearing. In the embodiment of FIG. 2B, the fastener 283 is fastened to the fastening area 290.

FIG. 2C illustrates an enlarged view of a portion of the first side of the disposable wearable absorbent article 210 of the embodiment of FIG. 2B. The fastener 283 is fastened to the fastening area 290, so that the first side ear 285 fastens the back 227 to the front 223. As a result, a portion of the first side ear 285 is disposed in the front 223 and a portion of the first side ear 285 is disposed in the back 227. In this fastened configuration, the front end location 252 is outside of the absorbent core area 226, in the front portion of the first side 281, laterally outboard from the longitudinal edge 224 of the absorbent core 225, and laterally outboard from the narrowest portion 222 of the chassis 220. In some embodiments, a front end location can be laterally inboard to the narrowest portion 222 of the chassis 220, and/or laterally inboard to the longitudinal edge 224 of the absorbent core 225, and/or outside of the front portion of the first side 281.

In the embodiment of FIG. 2C, the front end location 252 and the back end location 258 are both outside of the absorbent core area 226. However, in some embodiments, when an article is formed for wearing, a front end location can be disposed inside of the absorbent core area while a back end location can be disposed outside of the absorbent core area. In other embodiments, when an article is formed for wearing, a front end location can be disposed outside of the absorbent core area while a back end location can be disposed inside of the absorbent core area.

In various embodiments of the present disclosure, one or more parts of or at least a portion of the anchoring subsystem 270 can be structurally associated with the first side ear 285. In some embodiments, at least a portion of an anchoring subsystem, or substantially all of an anchoring subsystem, or even all of an anchoring subsystem, can be discrete from, or joined to, or attached to, or embedded in, or integral with a side ear. In various embodiments, at least a portion of the SAM 250, or substantially all of the SAM 250, or even all of the SAM 250, can be discrete from, or joined to, or attached to, or embedded in, or integral with the first side ear 285.

In embodiments in which one or more portions of the anchoring subsystem 270 are integral with the first side ear 285, the first side ear 285 can be considered to have a first portion, which includes the integral portions of the anchoring subsystem 270, and a second portion outside of the first portion. For example, if all of the SAM 250 is integral with the first side ear 285, then the first portion would include the SAM pathway 251, while the second portion would include the area of the first side ear 285 that is longitudinally outboard from the SAM pathway 251 as well as the area of the first side ear 285 that is longitudinally inboard to the SAM pathway 251. In such embodiments, this first portion and second portion can be configured in various ways, as described in connection with the embodiment of FIG. 1C.

In some embodiments, the disposable wearable absorbent article 210 can be configured such that one or more loads in the article can cause tension in the anchoring subsystem 270 before the load can cause tension in a portion of the first side ear that is outside of the anchoring subsystem 270. In various embodiments, the disposable wearable absorbent article 210 can be configured such that one or more loads in the article can cause greater tension in the anchoring subsystem 270 than in a portion of the first side ear that is outside of the anchoring subsystem 170.

In addition to the elements previously described, FIG. 2C also shows tension lines 275. The tension lines 275 illustrate how the SAM 150 can balance collected loads with obtained holding forces, so that the anchoring subsystem 270 can at least assist in holding the disposable wearable absorbent article 210 in place on a wearer. For example, the SAM 250 can collect loads at the front end 253, at the back end 259, and/or along the first SAM pathway 251. As a further example, the SAM 250 can also obtain holding forces the front end 253, at the back end 259, and/or along the first SAM pathway 251 as the SAM 250 experiences anchoring from direct or indirect contact with a wearer's body underneath the first SAM pathway 251.

These loads and forces can be received through various parts of the disposable wearable absorbent article 210, such as the chassis 220 and/or the first side ear 285. The anchoring subsystem 270 is configured to indirectly anchor the absorbent core 225 to a wearer, in that, while the SAM 250 is not directly connected to the absorbent core 225, and the SAM pathway 251 is disposed outside of the absorbent core area 226, loads from the absorbent core 225 can be transmitted through various parts of the disposable wearable absorbent article 210 to the SAM 250, which can balance collected loads with obtained holding forces, so that the anchoring subsystem 270 can at least assist in holding the disposable wearable absorbent article 210 in place on a wearer. As a result, the disposable wearable absorbent article 210 can feel comfortable, look attractive, and perform well as the article tends to stay in place on a wearer and not leak.

In addition to the embodiments of FIGS. 2A-2C, a front fastenable disposable wearable absorbent article can also include a SAM configured in various other ways, as described in US non-provisional patent applications entitled "Disposable Wearable Absorbent Articles with Anchoring Subsystems" filed on the same date as the present application and further identified by Ser. Nos. 12/204,844, 12/204,854, 12/204,858, and 12/204,864, each of which is incorporated by reference.

Modulus Mapping Method

The presence of one or more anchoring subsystem elements, such as a SAM, can be detected by using a modulus mapping method. This method can also be used to measure particular modulus of elasticity values for one or more anchoring subsystem elements, such as a SAM. The modulus mapping method is described below, and in connection with the embodiments of FIGS. 3A-3E.

A first step in the modulus mapping method is to determine an area of interest in a disposable wearable absorbent article. The area of interest is a continuous portion of the article, which completely contains the one or more anchoring subsystem elements to be tested. The area of interest also includes one or more portions of the article surrounding the anchoring subsystem element(s). In other words, the area of interest is not limited to the anchoring subsystem elements, but includes the one or more portions of the article that form the physical context on all sides of each of the element(s). The area of interest should contain enough of this physical context to be tested with the modulus mapping method on all sides of each of the anchoring system element(s). In this way, the presence of each of the anchoring subsystem element(s) can be detected within their physical context, in the area of interest.

The presence of an anchoring subsystem element may be known from knowledge of the article. In the example embodiment of FIGS. 3A-3E, a side panel 330 of a pant-type disposable wearable absorbent article is known to contain an anchoring subsystem with a SAM. Thus, for the modulus mapping method, the side panel 330 is the area of interest. Alternatively, the presence of an anchoring subsystem element may be apparent upon visual inspection of the article or may be suspected based on other facts. Where the presence of an anchoring subsystem element is uncertain, the area of interest can be determined by testing various portions of one or more samples of a disposable wearable absorbent article with the steps of the modulus mapping method, as will be understood by one of ordinary skill in the art.

A second step in the modulus mapping method is to cut the area of interest from the disposable wearable absorbent article. If the area of interest is a side panel of a disposable wearable absorbent article, then continuous cuts are made through the article along one or more paths between the side panel and the rest of the article. Any connections in the side panel are left fastened and/or intact, so the area of interest can be a continuous portion of the article.

If the area of interest is a side ear of a front fastenable disposable wearable absorbent article, then continuous cuts are made through the article along one or more paths between the side ear and the rest of the article. If the side ear is fastened, then it is unfastened, for complete removal from the article. For other areas of interest, including areas that are more than or less than a side panel or a side ear, continuous cuts are made through the article, on both sides of the area, from points on a waist edge of the article, cutting on paths perpendicular to the waist edge. These cuts either continue until they reach a leg opening of the article, or turn to reach the leg opening on the shortest cutting path parallel to the waist edge. Any connections in the area of interest are left fastened and/or intact, so the area of interest can be a continuous portion of the article.

A third step in the modulus mapping method is to mark the area of interest with a map, which is a grid of squares. While the area of interest is marked, the area is laid out flat, so the surface of the area of interest is not disturbed or distorted. In general, the gridlines of the map should run parallel to and perpendicular to the lateral direction of the disposable wearable absorbent article. However, if the material of the area of interest has a primary direction of elasticity, stretchability, or extensibility, then the gridlines of the map should run parallel to and perpendicular to that primary direction of stretch. Each of the squares in the grid is 5.0 millimeters by 5.0 millimeters. The gridlines can be measured in various ways, such as by using a calibrated ruler. The gridlines can also be marked in various ways, such as by using a fine tipped marking pen. The marked map is a grid of squares with rows R1 through Rn and columns C1 through Cn. Thus, each square on the map can be uniquely referenced by row and column number (e.g. C1:R1 for the square of column 1, row 1).

Figure 3A:
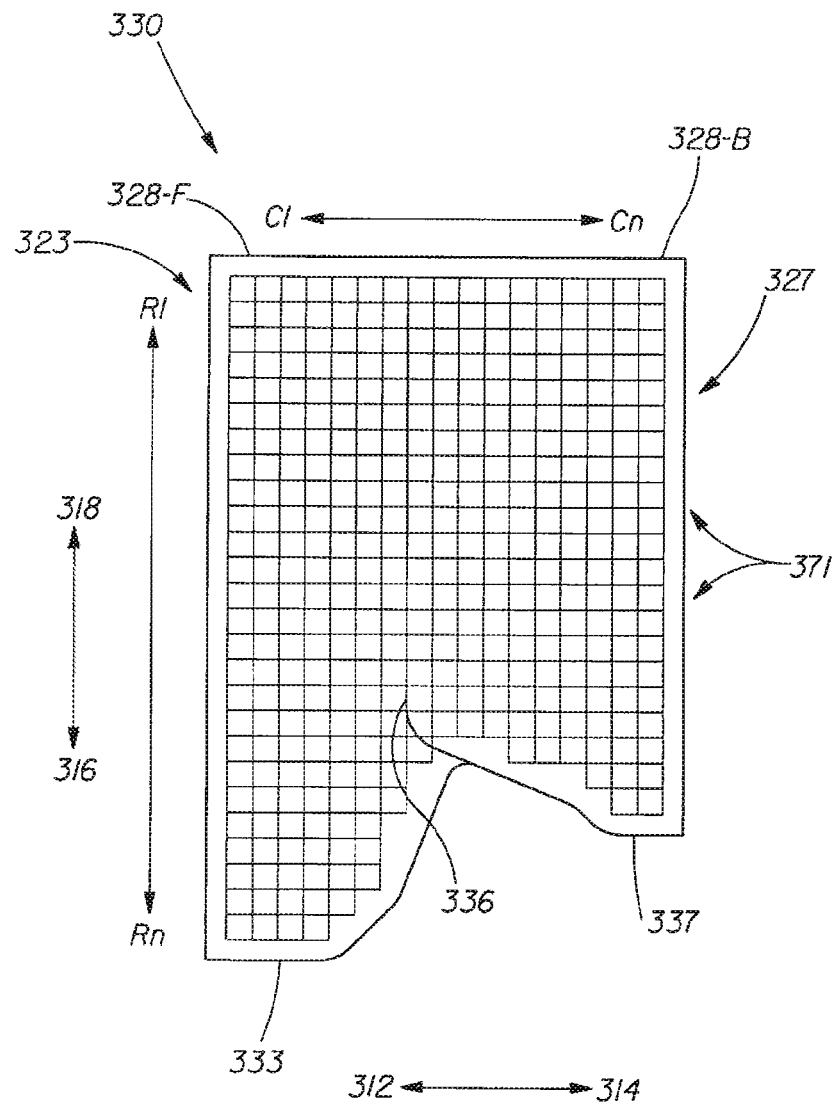
FIG. 3A illustrates an enlarged view of a side panel of a disposable wearable absorbent article, cut from the article and marked with a map for testing with a modulus mapping method, according to embodiments of the present disclosure.
Figure 3B:
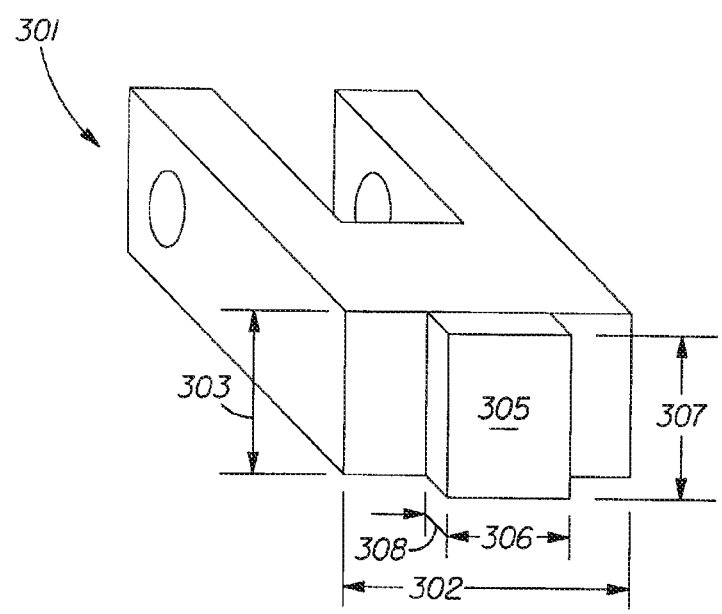
FIG. 3B illustrates a modified pneumatic grip, for use in the modulus mapping method according to embodiments of the present disclosure.

FIG. 3A illustrates an enlarged view of a portion of the side panel 330 of the disposable wearable absorbent article, cut from the article and marked with a map 371, for testing with the modulus mapping method. FIG. 3A illustrates directions of laterally inboard 312 and laterally outboard 314 (using the lateral directions for a back 327 of the article for ease of reference) as well as directions for longitudinally inboard 316 and longitudinally outboard 318. The portion of the side panel 330 includes a portion of the back 323, a portion of the front 327, a front waist edge 328-F, a back waist edge 328-B, a front portion of the side panel 333, a connection 336, and a back portion of the side panel 337. In the embodiment of FIG. 3A, the material of the area of interest has a primary direction of stretchability in the lateral direction. Therefore, the map 371 is marked on the side panel 330, as described above, so that the gridlines of the map 371 run parallel to and perpendicular to that primary direction of stretch, which is the lateral direction.

A fourth step in the modulus mapping method is to test the area of interest. The dimensions of the area of interest are measured and recorded, for use in calculating modulus of elasticity. To determine thickness of material, a 3.14 cm2 round foot caliper is used, with 0.5 kPa of pressure and 10 seconds of residence time. The testing uses a constant rate of extension tensile tester, fitted with a 5 N load cell. The tensile tester includes a computer interface, such as a MTS Alliance with TestWorks 4 software (available from MTS Systems Corp., Eden Prairie, Minn.). With regard to the test equipment described below, dimensions are given as precise values.

The tensile tester is fitted with a set of 10 N Advantage™ pneumatic grips (available from MTS as part 100-032-017) and 15 millimeter wide by 8 millimeter high 10 N Advantage™ grip faces with smooth steel surface (available from MTS as part 56-163-702). Each of the grip faces is modified by mounting a hard rubber facing on the grip face. The rubber facing is a hard neoprene rubber with a Durometer rating of 70 A. The rubber facing is 5.00 millimeters wide by 8.0 millimeters high by 2.0 millimeters deep. The rubber facing is centered on the base width of the grip face. When the pneumatic grips are closed, the rubber facings should be vertically and horizontally aligned.

Figure 3C:
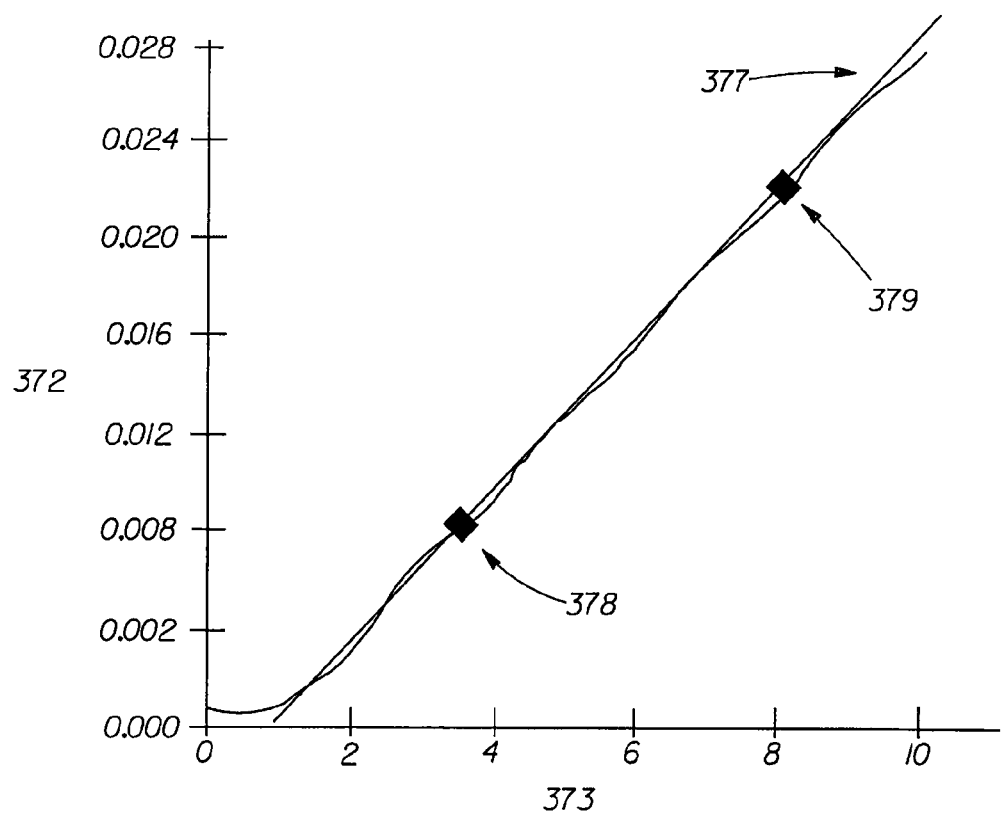
FIG. 3C illustrates an exemplary graph of the modulus of elasticity of a square of the map of the embodiment of FIG. 3A, according to embodiments of the present disclosure.

FIG. 3C illustrates a modified pneumatic grip 301, as described above, for use in the modulus mapping method. The modified pneumatic grip 301 includes base grip width 302 (15 millimeters) and base grip height 303 (8 millimeters). The modified pneumatic grip 301 also includes a hard rubber facing 305 with a facing width 306 (5.00 millimeters), a facing height 307 (8.0 millimeters), and a facing depth 308 (2.0 millimeters).

Using this test equipment, the area of interest is tested with the modulus mapping method as follows. For clarity, in this description of testing, references to the area of interest refer to the side panel 330 of the embodiment of FIG. 3A. The data acquisition rate of the tensile tester is set to 100 Hz and the gage length is set to 5.0 mm. The crosshead and the load cell are zeroed. If there is no primary direction of elasticity, stretchability, or extensibility in the area of interest, then the area of interest is inserted and aligned as described below. The area of interest is inserted into the upper pneumatic grip at the square C1:R1 and oriented to pull the side panel 330 in the lateral direction of the disposable wearable absorbent article. The upper grip is aligned outside of square C1:R1, along the laterally outboard gridline of the square C1:R1, and closed. The area of interest is also inserted into the lower pneumatic grip, aligned outside of square C1:R1, along the laterally inboard gridline of the square, and closed.

If there is a primary direction of elasticity, stretchability, or extensibility in the area of interest, then the area of interest is inserted and aligned as described below. The area of interest is inserted into the upper pneumatic grip at the square C1:R1 and oriented to pull the side panel 330 in the primary direction of stretch. The upper grip is aligned outside of square C1:R1, along a first gridline of the square that is perpendicular to the primary direction of stretch, and closed. The area of interest is also inserted into the lower pneumatic grip, aligned outside of square C1:R1, along a second gridline of the square that is opposite from the first gridline and also perpendicular to the primary direction of stretch, and closed.

The area of interest should be under enough tension to eliminate any slack, but with less than 0.02 N of force on the load cell. The tensile tester is started and data is collected. The grips are moved apart at a constant rate of 25 millimeters per minute to 10% strain. The modulus of elasticity of the square is calculated as a directional modulus of elasticity, since the area of interest is pulled in a particular direction, e.g. the lateral direction or the primary direction of stretch. The directional modulus of elasticity of the square is calculated as the slope of the linear region of the resulting stress versus strain curve, using a slope segment length of 50% to determine the modulus line.

As an example, FIG. 3C illustrates an exemplary graph of the modulus of elasticity of a square of the map 371, with stress 372 in mega Pascals versus strain 373 as a percentage, and a modulus line 377 using a slope segment length of 50% from point 378 to point 379. The directional modulus of elasticity is determined to ±0.01 mega Pascals and recorded. This testing procedure is repeated for each square on the map, testing the first column (from C1:R1 to C1:Rn) followed by each successive column (from C2 to Cn).

FIG. 3D illustrates an exemplary chart with directional modulus of elasticity values in mega Pascals, obtained from the modulus mapping method testing and recorded for each square of the map 371 of the area of interest, which is the side panel 330 of the disposable wearable absorbent article.

A fifth step in the modulus mapping method is to plot and evaluate the directional modulus of elasticity values obtained from the modulus mapping method testing. The directional modulus of elasticity values are transferred to a spreadsheet such as Microsoft Excel™ and plotted as a surface contour plot. For the plot, set the maximum Z-axis value to truncate high modulus values resulting from seams, chassis bonds, and/or other such structural discontinuities in the area of interest that are unrelated to anchoring subsystem element(s). As an example, a maximum value of approximately three and a half times the upper value of the directional modulus of elasticity in the lowest modulus region is useful for the directional modulus of elasticity values in the embodiment of FIG. 3D.

Choose major value intervals to visually evaluate the plot for existing patterns of high and low directional modulii of elasticity in the area of interest. A minimum of five intervals should be used for this evaluation. For example, an interval value of approximately 0.29 mega Pascals is useful for the directional modulus of elasticity values in the embodiment of FIG. 3D. One skilled in the art of visual pattern recognition will understand that these values are representative and can be determined empirically for a given set of directional modulus of elasticity values.

Figure 3E:
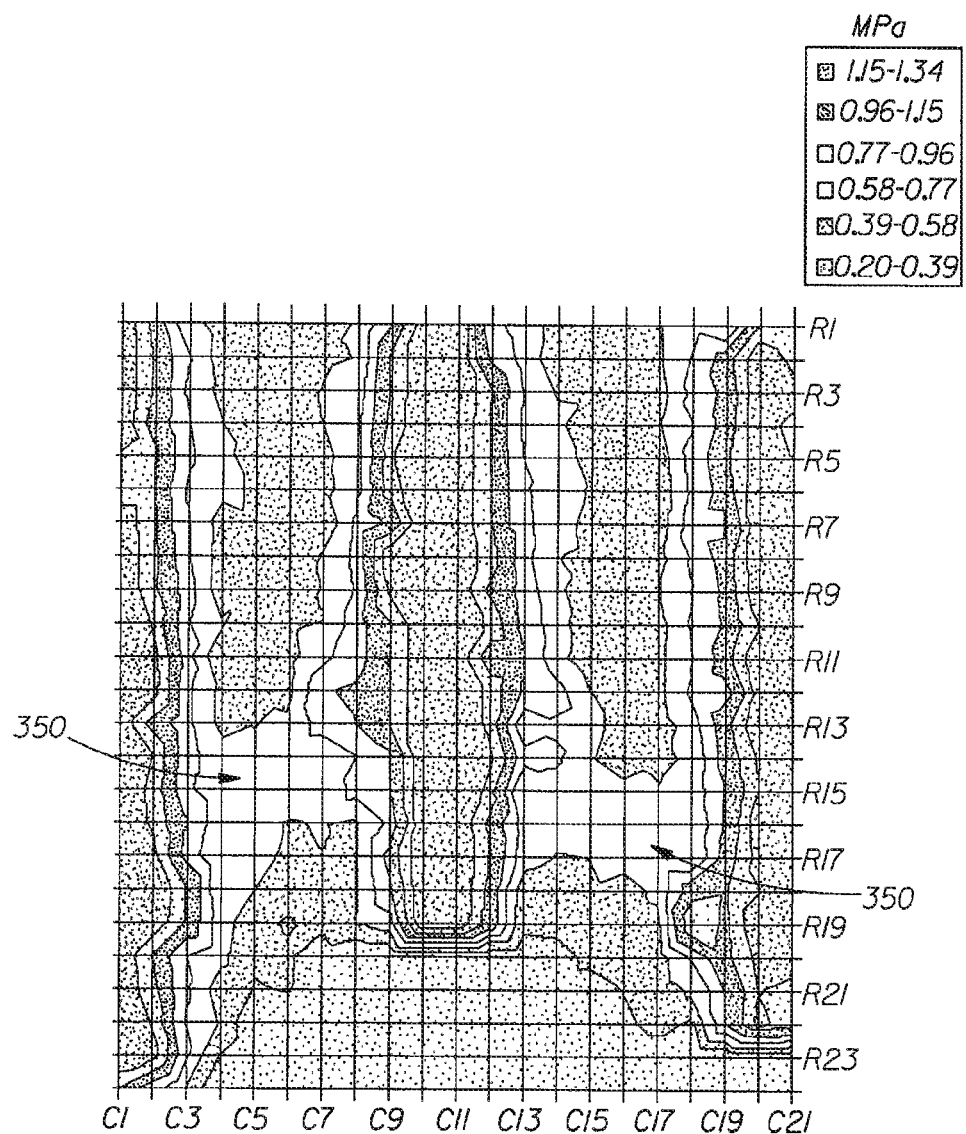
FIG. 3E illustrates an exemplary surface contour plot of the modulus of elasticity values of the chart of the embodiment of FIG. 3D, according to embodiments of the present disclosure.

FIG. 3E illustrates an exemplary surface contour plot of the directional modulus of elasticity values of the chart of the embodiment of FIG. 3D, as described above, for use in the modulus mapping method. In FIG. 3E, the maximum Z-axis values are truncated at 1.39 mega Pascals, which is three and half times the upper value of the directional modulus of elasticity in the lowest modulus region (e.g. 0.39 mega Pascals). The major value intervals are chosen to be 0.29 mega Pascals.

One skilled in the art of visual pattern recognition will recognize that the plot of FIG. 3E illustrates the presence of an anchoring subsystem with exactly one SAM 350. The size and/or shape of the SAM 350 in the example embodiment of FIGS. 3A-3E may or may not correspond with other embodiments of the present disclosure. However, the modulus mapping method can be used to detect the presence of embodiments of SAMs of the present disclosure, as will be understood by one of ordinary skill in the art. Further, the plot of FIG. 3E indicates that the SAM has a directional modulus of elasticity between 0.58 and 0.77 mega Pascals. The one SAM 350 extends through a side connection in the side panel. Thus, the modulus mapping method can be used to detect the presence of one or more anchoring subsystem elements and to measure particular directional modulus of elasticity values for such elements.

Embodiments of the present disclosure include disposable wearable absorbent articles with anchoring subsystems that fit wearers well. The designs of these articles help prevent the articles from sagging or slipping down on a wearer. As a result, the disposable wearable absorbent articles of the present disclosure can feel comfortable, look attractive, and perform well as the articles tend to stay in place on wearers and not leak.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm", is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable wearable fastenable absorbent article having a lateral centerline, that when in an unfastened state comprises:
    an absorbent core area;
    a side, comprising a front portion and a back portion; and
    an anchoring subsystem contained within a particular, defined area of the disposable wearable absorbent article, said defined area being the side; where said anchoring subsystem includes exactly one side anchoring member, wherein the entire side anchoring member is embedded, partly in the front portion of the side and partly in the back portion of the side;
    wherein when the article is in an unfastened state, no part of the side anchoring member crosses the lateral centerline, and wherein the side anchoring member includes:
    a pathway;
    a front end of the pathway disposed at a front end location at a front end longitudinally outboard distance;
    a back end of the pathway disposed at a back end location at a back end longitudinally outboard distance; and
    a middle disposed along the pathway between the front end and the back end, including a middle location disposed at a middle longitudinally outboard distance;
    wherein:
        at least one of the front end location and the back end location is outside of the absorbent core area;
        the back end longitudinally outboard distance is less than the front end longitudinally outboard distance; and
        the front end longitudinally outboard distance is about equal to the middle longitudinally outboard distance;
        and wherein the side anchoring member does not substantially encircle a leg of a wearer when the article is worn by the wearer.

2. The disposable wearable absorbent article of claim 1, wherein:
    the article is a pant-type article;
    the article includes a front;
    the side is a side panel, with a front portion in the front, wherein the front portion includes a laterally inboard edge; and
    the front end location is proximate to the laterally inboard edge.

3. The disposable wearable absorbent article of claim 1, wherein:
    the article is a pant-type article;
    the article includes a back;
    the side is a side panel, with a back portion in the back, wherein the back portion includes a laterally inboard edge; and
    the back end location is proximate to the laterally inboard edge.

4. The disposable wearable absorbent article of claim 1, wherein:
    the side includes a side ear panel, which includes the side anchoring member and a fastener; and
    the front end location is proximate to the fastener.

5. The disposable wearable absorbent article of claim 1, wherein:
    the side includes a first portion and a second portion, outside of the first portion;
    substantially all of the side anchoring member is disposed within the first portion;
    substantially all of the first portion is configured to have a higher directional modulus of elasticity; and
    substantially all of the second portion is configured to have one or more lower directional moduli of elasticity.

6. The disposable wearable absorbent article of claim 5, wherein the higher directional modulus of elasticity is at least ten percent greater than any of the one or more lower directional moduli of elasticity.

7. The disposable wearable absorbent article of claim 1, wherein:
    the side includes a first portion and a second portion, outside of the first portion;
    substantially all of the side anchoring member is disposed within the first portion;
    substantially all of the first portion is incrementally stretched to a lesser degree; and
    substantially all of the second portion is incrementally stretched to one or more greater degrees.

8. The disposable wearable absorbent article of claim 1, wherein:
    the side includes a first portion and a second portion, outside of the first portion;
    substantially all of the side anchoring member is disposed within the first portion;
    one or more unstretched areas are distributed throughout substantially all of the first portion; and substantially all of the second portion is incrementally stretched.

9. The disposable wearable absorbent article of claim 1, wherein:
the side includes a first portion and a second portion, outside of the first portion;
substantially all of the side anchoring member is disposed within the first portion; and
one or more over-bonded areas are distributed throughout substantially all of the first portion.

10. The disposable wearable absorbent article of claim 1, wherein:
the side includes a first portion and a second portion, outside of the first portion;
substantially all of the side anchoring member is disposed within the first portion;
substantially all of the first portion is configured to have a higher force per unit width at a particular strain; and
substantially all of the second portion is configured to have one or more lower force per unit width at the particular strain.

11. The disposable wearable absorbent article of claim 1, wherein:
the side includes a first portion and a second portion, outside of the first portion;
substantially all of the side anchoring member is disposed within the first portion;
substantially all of the first portion includes a higher caliper elastomer; and
substantially all of the second portion includes one or more lower caliper elastomers.

12. The disposable wearable absorbent article of claim 1, wherein:
the side includes a first portion and a second portion, outside of the first portion;
substantially all of the side anchoring member is disposed within the first portion;
the first portion is incrementally stretched with a first particular number of teeth per a unit of distance; and
the second portion is incrementally stretched with a second particular number of teeth per the unit of distance, wherein the first particular number of teeth is less than the second particular number of teeth.

13. The disposable wearable absorbent article of claim 1, wherein:
the side includes a first portion and a second portion, outside of the first portion;
substantially all of the side anchoring member is disposed within the first portion;
substantially all of the first portion includes a higher performance elastomer; and
substantially all of the second portion includes one or more lower performance elastomers.

14. The disposable wearable absorbent article of claim 1, wherein:
the side anchoring member has an overall length; and
the side anchoring member has a substantially uniform width over the entire overall length.

15. The disposable wearable absorbent article of claim 1, wherein an overall shape of a portion of the pathway between the middle and the back end is curved.

16. The disposable wearable absorbent article of claim 1, wherein the side anchoring member is configured as a geodesic.

* * * * *